US006232104B1

(12) United States Patent
Lishanski et al.

(10) Patent No.: US 6,232,104 B1
(45) Date of Patent: May 15, 2001

(54) DETECTION OF DIFFERENCES IN NUCLEIC ACIDS BY INHIBITION OF SPONTANEOUS DNA BRANCH MIGRATION

(75) Inventors: Alla Lishanski, San Jose; Marc Taylor, Mountain View; Nurith Kurn, Palo Alto, all of CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/376,097

(22) Filed: Aug. 17, 1999

(51) Int. Cl.[7] .............................. C12P 19/34; C12Q 1/68; C07H 21/04

(52) U.S. Cl. .......................... 435/91.2; 435/6; 536/23.1; 536/24.2; 536/24.33

(58) Field of Search ..................... 435/6, 91.2; 536/23.1, 536/24.2, 24.33

(56) References Cited

U.S. PATENT DOCUMENTS

| | | | |
|---|---|---|---|
| 4,683,202 | 7/1987 | Mullis | 435/91 |
| 5,035,996 | 7/1991 | Hartley | 435/6 |
| 5,187,066 | 2/1993 | Becker et al. | 435/7.36 |
| 5,314,809 | * 5/1994 | Erlich et al. | 435/91.2 |
| 5,340,728 | 8/1994 | Grosz et al. | 435/91.2 |
| 5,422,252 | * 6/1995 | Walker et al. | 435/91.2 |

(List continued on next page.)

FOREIGN PATENT DOCUMENTS

| | | |
|---|---|---|
| 164876 A1 | 12/1985 | (EP) . |
| 450370 A1 | 10/1991 | (EP) . |
| 469 755 A1 | 2/1992 | (EP) . |
| WO 93/10267 | 5/1993 | (WO) . |
| WO 94/03812 | 2/1994 | (WO) . |

OTHER PUBLICATIONS

Panyutin et al., *The kinetics of spontaneous DNA branch migration*, Proc. Natl. Acad. Sci. USA, 91:2021–2025, 1994.

(List continued on next page.)

*Primary Examiner*—W. Gary Jones
*Assistant Examiner*—B J Forman
(74) *Attorney, Agent, or Firm*—Patrick G Gattari

(57) ABSTRACT

A method is disclosed for detecting the presence of a difference between two related nucleic acid sequences. In the method a complex is formed comprising both strands of each sequence. Each member of at least one pair of non-complementary strands within the complex have labels. The association of the labels as part of the complex is determined as an indication of the presence of a difference between the two related sequences. The complex generally comprises a Holliday junction. In one aspect a medium suspected of containing said two related nucleic acid sequences is treated to provide partial duplexes having non-complementary tailed portions at one end. The double stranded portions of the partial duplexes are identical except for said difference. One of the strands of one of the partial duplexes is complementary to one of the strands of the other of the partial duplexes and the other of the strands of one of the partial duplexes is complementary to the other of the strands of the other of the partial duplexes. The medium is subjected to conditions that permit the binding of the tailed portions of the partial duplexes to each other. If there is a difference in the related nucleic acid sequences, a stable complex is formed comprising a Holliday junction. If no difference exists, the complex dissociates into duplexes. A determination is made whether the stable complex is formed, the presence thereof indicating the presence of the related nucleic acid sequences. The method has application in detecting the presence of a mutation in a target sequence or in detecting the target sequence itself. Also provided is an alternative primer scheme which allows for the reduction of background signal due to mis-priming during amplification of the nucleic acid sequences in the detection method described herein.

27 Claims, 9 Drawing Sheets

U.S. PATENT DOCUMENTS

| | | | |
|---|---|---|---|
| 5,427,929 | 6/1995 | Richards et al. | 435/91.2 |
| 5,470,724 | 11/1995 | Ahern | 435/91.2 |
| 5,474,916 | 12/1995 | Reischl et al. | 435/91.2 |
| 5,480,783 | 1/1996 | Haff | 435/91.2 |
| 5,508,178 | 4/1996 | Rose et al. | 435/91.1 |
| 5,512,441 | 4/1996 | Ronai | 435/91.2 |
| 5,525,462 | 6/1996 | Takarada et al. | 435/6 |
| 5,525,494 | 6/1996 | Newton | 435/91.2 |
| 5,532,126 | 7/1996 | Chu et al. | 435/6 |
| 5,554,516 | 9/1996 | Kacian et al. | 435/91.21 |
| 5,554,517 | 9/1996 | Davey et al. | 435/91.21 |
| 5,556,773 | 9/1996 | Yourno | 435/91.2 |
| 5,561,044 | 10/1996 | Walker et al. | 435/6 |
| 5,580,730 | 12/1996 | Okamoto | 435/6 |
| 5,582,981 | 12/1996 | Toole et al. | 435/6 |
| 5,593,840 | 1/1997 | Bhatnagar et al. | 435/6 |
| 5,599,674 | 2/1997 | Pena et al. | 435/6 |
| 5,616,464 | 4/1997 | Albagli et al. | 435/6 |
| 5,624,825 | 4/1997 | Walker et al. | 435/91.2 |
| 5,654,143 | 8/1997 | Mallet et al. | 435/6 |
| 5,665,572 | 9/1997 | Ikeda et al. | 435/91.2 |
| 5,679,522 | 10/1997 | Modrich et al. | 435/6 |
| 5,681,705 | 10/1997 | Schram et al. | 435/6 |
| 5,710,029 | 1/1998 | Ryder et al. | 435/91.1 |
| 5,712,386 | 1/1998 | Wang et al. | 536/24.33 |
| 5,736,365 | 4/1998 | Walker et al. | 435/91.2 |
| 5,741,678 | 4/1998 | Ronai | 435/91.2 |
| 5,744,308 | 4/1998 | Guillou-Bonnici et al. | 435/6 |
| 5,766,849 | 6/1998 | McDonough et al | 435/6 |
| 5,780,231 | 7/1998 | Brenner | 435/6 |
| 5,783,391 | 7/1998 | Rossi | 435/6 |
| 5,817,465 | 10/1998 | Mallet et al. | 435/6 |
| 6,013,439 * | 1/2000 | Lishanski et al. | 435/6 |

OTHER PUBLICATIONS

Cardullo et al., *Detection of nucleic acid hybridization by nonradiative fluorescence resonance energy transfer*, Biochemistry, 85:8790–8794, 1988.

Mueller et al., *T 4 endonuclease VII cleaves the crossover strands of Holiday junction analogs*. Proc. Natl. Acad. Sci. USA, 85:9441–9445, 1988.

Panyutin et al., *Formation of a Single Base Mismatch Impedes Spontaneous DNA Branch Migration*, J. Mol. Biol., 230:413–424, 1993.

Birch, *Simplified hot start PCR*, Nature, 381:445–446, 1996.

Porter–Jordan et al., *Nested Polymerase Chain Reaction Assay for the Detection of Cytomegalovirus Overcomes False Positives Caused by Contamination With Fragmented DNA*, Journal of Medical Virology, 30:85–91, 1990.

Gyllensten et al., *Generation of single–stranded DNA by the polymerase chain reaction and its application to direct sequencing of the HLA–DQA locus*, Proc. Natl. Acad. Sci. USA, 85:7652–7656, 1988.

Erlich et al., *Recent Advances in the Polymerase Chain Reaction*, Science, 252:1643–1651, 1991.

Rimstad et al., *Identification of a Double–Stranded RNA Virus by Using Polymerase Chain Reaction and Magnetic Seperation of the Synthesized DNA Segments*, Journal of Clinical Microbiology, 28 No. 10:2275–2278, 1990.

Joseph Yourno, *A Method for Nested PCR with Single Closed Reaction Tubes*, PCR Methods and Applications, 2:61–65, 1992.

* cited by examiner

DETECTION OF DIFFERENCES IN NUCLEIC ACIDS BY INHIBITION OF SPONTANEOUS DNA BRANCH MIGRATION

FIELD OF THE INVENTION

This invention relates to the detection of differences between nucleic acid sequences including the detection of mutations and single nucleotide polymorphisms. The present invention is suitable for use in environmental and diagnostic testing due to the convenience with which is can be practiced.

BACKGROUND OF THE INVENTION

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labeling of DNA with T4 polynucleotide kinase has made it possible to identify, isolate, and characterize various nucleic acid sequences of biological interest.

Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the above method is slow and labor intensive, and nonisotopic labels that are less readily detected than radiolabels are frequently not suitable.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the hybridization sites on the DNA sequence complementary to the 5' ends of the oligonucleotide primers.

Other methods for amplifying nucleic acids are single primer amplification, ligase chain reaction (LCR), nucleic acid sequence based amplification (NASBA) and the Q-beta-replicase method. Regardless of the amplification used, the amplified product must be detected.

Genetic recombination involves the exchange of DNA strands between two related DNA duplexes. The branch point between two duplex DNAs that have exchanged a pair of strands is thought to be an important intermediate in homologous recombination. This branch point is otherwise referred to as the Holliday junction. Movement of the Holliday junction by branch migration can increase or decrease the amount of genetic information exchanged between homologues. In vivo strand exchange is protein mediated, unlike the spontaneous migration that occurs in vitro.

There is a great demand for simple universal high-throughput methods for detection of differences in related nucleic acid sequences regardless of the exact nature of the difference. This demand is becoming more and more urgent due to the ongoing rapid discovery of new disease related mutations brought about by the progress of the Human Genome Project. A detection method for mutations that is not dependent on the exact location of the mutation is valuable in the case of diseases that are known to result from various mutations within a given sequence. Moreover, such a method will be useful for verification of sequence homology as related to various applications in molecular biology, molecular medicine and population genetics.

Some of the current methods are either targeted for sets of known mutations, such as, for example, the Reverse Dot Blot method, or involve gel-based techniques, such as, for example, single stranded conformational polymorphism (SSCP), denaturing gradient gel electrophoresis (DGGE) or direct sequencing as well as a number of methods for the detection of heteroduplexes. Accordingly, such methods are laborious and time consuming.

Various methods for mutation detection have been developed in the recent years based on amplification technology. The detection of sequence alterations is based on one of the following principles: allele-specific hybridization, chemical modification of mismatched bases with subsequent strand cleavage, nuclease cleavage at mismatches, recognition of mismatches by specific DNA binding proteins, changes in electrophoretic mobility of mismatched duplexes in gradients of denaturing agents, conformation-induced changes in electrophoretic mobility of single-stranded DNA sometimes combined with conformation-specific nuclease cleavage. Some of these methods are too laborious and time-consuming and many depend on the nature of base alteration.

It is desirable to have a sensitive, simple, inexpensive method for detecting differences in nucleic acids such as mutations, preferably, in a homogeneous format. The method should minimize the number and complexity of steps and reagents. Such a method would be suitable for a large scale population screening.

DESCRIPTION OF THE RELATED ART

Formation of a single base mismatch that impedes spontaneous DNA branch migration is described by Panyutin, et al., (1993) *J. Mol. Biol.*, 230:413–424.

The kinetics of spontaneous DNA branch migration is discussed by Panyutin, et al., (1994) *Proc. Natl. Acad. Sci. USA*, 91: 2021–2025.

The mechanism of inhibition of spontaneous DNA branch migration by mismatches is further discussed in Biswas et al. (1998) *J. Mol. Biol.*, 279, 795–806.

Detection of the stable cruciform structures, indicating sequence alteration in the test sequence relative to a reference sequence, using streptavidin coated microtiter plates and an enzyme anti-digoxin monoclonal antibody conjugate is described in Lishanski et al. 1996, A homogenous mutation detection method based on inhibition of branch migration, Abstract of the 28th Annual Oakridge Conference on Advanced Analytical Concepts for the Clinical Laboratory, "Tomorrow's Technology Today", p. 15. Detection of sequence alterations using branch migration inhibition in a luminescent oxygen channeling assay (LOCI) format is shown in WO 97123646.

European Patent Application No. 0 450 370 A1 (Wetmur, et al.,) discloses branch migration of polynucleotides.

A displacement polynucleotide assay method and polynucleotide complex reagent therefor is discussed in U.S. Pat. No. 4,766,062 (Diamond, et al.,).

A strand displacement assay and complex useful therefor is discussed in PCT application WO 94/06937 (Eadie, et al.,).

PCT application WO/86/06412 (Fritsch, et al.,) discusses process and nucleic acid construct for producing reagent complexes useful in determining target nucleotide sequences.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, et al., *Science* (1988) 239:487.

U.S. Pat. No. 4,683,202 (Mullis) shows a staged method of PCR in which a second set of primers is used to amplify a smaller DNA sequence contained within the DNA sequence amplified by a first primer set. This method, commonly referred to as nested PCR, is recognized as a more sensitive and specific method. See U.S. Pat. Nos. 5,556,773 (Yourno) and 5,340,728 (Grosz et al.) and Gyllensten U.B., et al., Generation of single-stranded DNA by the polymerase chain reaction and its application to direct sequencing of the HLA-DQA locus, *Proc. Nat. Acad. Sci. USA*, 85:7652–56 (1998); Yourno J, A Method of Nested PCR with Single Closed Reaction Tubes, *PCR Methods and Applications*, 2:60–65 (1992); Rimstad E. et al., Identification of a Double-Stranded RNA Virus by Using Polymerase Chain Reaction and Magnetic Separation of the Synthesized DNA Segments, *J. Clin. Micro.* 28:2275–78 (1990); Erlich H. A. et al., Recent Advances in Polymerase Chain Reaction, *Science*, 252:1643–50 (1991); Porter-Jordan et al., Nested Polymerase Chain Reaction Assay for the Detection of Cytomegolovirus Overcomes False Positives Caused by Contamination with Fragmented DNA, *J. Med. Vir.*, 30:85–91 (1990).

SUMMARY OF THE INVENTION

The present invention provides for method for detecting the presence of a mutation in a target nucleic acid sequence, or the presence of a difference between a target nucleic acid and a reference nucleic acid, which minimizes the effect of false priming in the amplification reactions of the present invention. The method comprises the amplification of target and reference nucleic acid sequences by polymerase chain reaction using primers P2, P4 and P5. Primer P4 has a 3'-end region Pa that is capable of hybridizing to the target or reference and a 5'-end region T that is not complementary to the target or reference. Primer P5 is capable of hybridizing to the target or reference at a location in the 3'-direction of the sequence capable of hybridizing the 3' region of primer P4. Either primer P2 is a mixture of P2 with a first label and P2 with a second label, or P4 has a first label and P5 has a second label. Following amplification, tailed partial duplexes of the reference and target sequences are formed. The tailed partial duplexes have tails of non-complementary strands where the first strand is the sequence of P5 or its complement and the second strand is T or its complement. A quadramolecular complex is formed by the hybridization of complementary tails on the two partial duplexes where the complex has at least one pair of non-complementary strands and each of the strands has a label. Detection of the association of the labels as part of the complex is related to the presence of the difference between the target and reference sequences.

The 3' portion of primer P4 may hybridize to the target nucleic acid sequence at a sequence adjacent to the sequence hybridizable to primer P5, but such sequences need not be adjacent. The sequences may partially overlap or be separated in sequence by a gap. Amplification of the target and reference sequences can proceed in the same or different reaction vessels.

Another embodiment of the present invention is a method of preparing partial duplexes having two predefined non-complementary single stranded sequences. The method includes combining in a medium a polymerase, nucleoside triphosphates and primers P2, P4 and P5. The medium is subjected to temperature cycling to form the partial duplexes.

Another embodiment of the present invention is a method of preparing partial duplexes having two predefined non-complementary single stranded sequences. The method includes combining in one medium a sample containing a target nucleic acid sequence, a polymerase, nucleotide triphosphates and primers P2 and P4, and combining a second medium, a target nucleic acid sequence, a polymerase, nucleotide triphosphates, and primers P2 and P5. The combinations are subjected to temperature cycling. The media are combined and the combination is subjected to conditions resulting in denaturation and reassociation of the single stranded amplification products to form the partial duplexes.

A further embodiment of the present invention is quadramolecular complex made by the process of amplifying a target nucleic acid sequence having a mutation and a reference nucleic acid sequence using primers P2, P4 and P5. The tail sequences of the tailed partial duplexes formed by the amplification reaction are hybridized to form the quadramolecular complex.

Another embodiment of the present invention is a kit for the detection of a difference between a target nucleic acid sequence and a reference nucleic acid sequence, or the presence of mutation in a nucleic acid sequence. A kit in accordance with the present invention comprises in packaged combination primer primer P2, primer P4 and primer P5 as described above, and further comprises a polymerase, nucleotide triphosphates, a reference nucleic acid sequence and buffer reagents sufficient to conduct nucleic acid amplification by polymerase chain reaction. The primers may be associated with labels. The primers may be contained in separate packages in various combinations.

DESCRIPTION OF THE SPECIFIC EMBODIMENTS

Figure 1A:
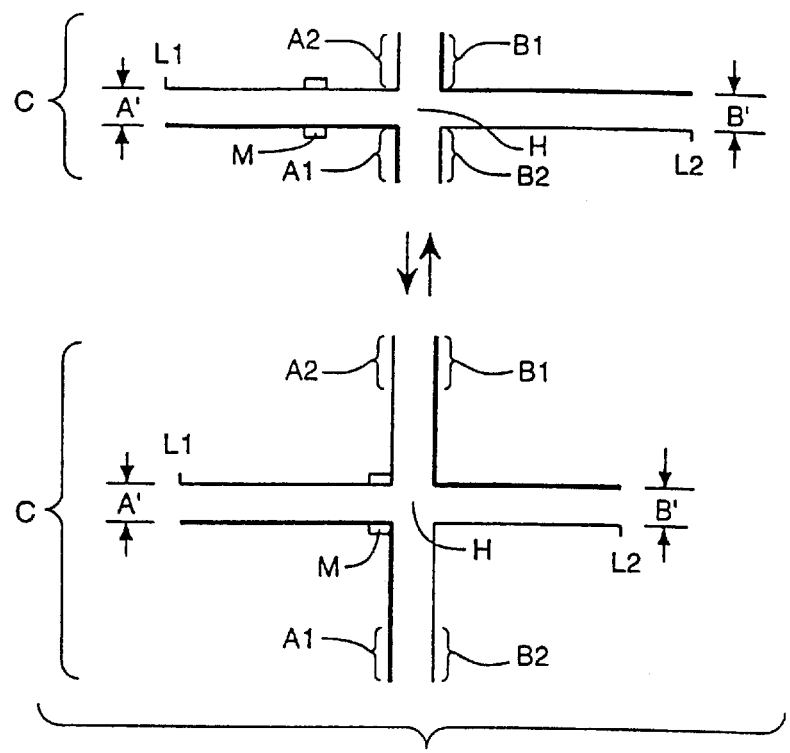
FIGS. 1A and 1B are schematic diagrams depicting branch migration in the quadramolecular complex of the present invention.

The present invention is universal and permits detection of any difference in two related nucleic acid sequences, whether or not such difference is known. Such differences include any mutation including single base substitution, deletion or insertion within a sequence that can be defined by a pair of primers for conducting the polymerase chain reaction. The method may be homogeneous or heterogeneous, non-radioactive, fast and amenable to automation. It is ideally suited for rapid mutation pre-screening. The invention also has application in the area of amplification by polymerase chain reaction. The present invention permits PCR and subsequent steps, such as detection of the PCR products, to be conducted without the need for additional probes in a single container without a separation step.

In one aspect the present method involves formation of a four-strand cruciform DNA structure or complex. The formation involves producing partial duplexes by amplification by using three different primers in the polymerase chain reaction and allowing the amplification products to anneal. The complex dissociates into normal duplex structures by strand exchange by means of branch migration when the double stranded portions of each partial duplex are identical. However, where there is a difference between the two double stranded portions, the complex does not dissociate and can be detected as an indication of the presence a difference between the nucleic acids.

Before proceeding further with a description of the specific embodiments of the present invention, a number of terms will be defined.

Definitions

Nucleic acid—a compound or composition that is a polymeric nucleotide or polynucleotide. The nucleic acids include both nucleic acids and fragments thereof from any source, in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The nucleic acid can be only a minor fraction of a complex mixture such as a biological sample. The nucleic acid can be obtained from a biological sample by procedures well known in the art. Also included are genes, such as hemoglobin gene for sickle-cell anemia, cystic fibrosis gene, oncogenes, cDNA, and the like. Where the nucleic acid is RNA, it is first converted to cDNA by means of a primer and reverse transcriptase. The nucleotide polymerase used in the present invention for carrying out amplification and chain extension can have reverse transcriptase activity. Sequences of interest may be embedded in sequences of any length of the chromosome, cDNA, plasmid, etc.

Sample—the material suspected of containing the nucleic acid. Such samples include biological fluids such as blood, serum, plasma, sputum, lymphatic fluid, semen, vaginal mucus, feces, urine, spinal fluid, and the like; biological tissue such as hair and skin; and so forth.

Other samples include cell cultures and the like, plants, food, forensic samples such as paper, fabrics and scrapings, water, sewage, medicinals, etc. When necessary, the sample may be pretreated with reagents to liquefy the sample and release the nucleic acids from binding substances. Such pretreatments are well known in the art.

Amplification of nucleic acids—any method that results in the formation of one or more copies of a nucleic acid. One such method for enzymatic amplification of specific sequences of DNA is known as the polymerase chain reaction (PCR), as described by Saiki, et al., supra. This in vitro amplification procedure is based on repeated cycles of denaturation, oligonucleotide primer annealing, and primer extension by thermophilic template dependent polynucleotide polymerase, resulting in the exponential increase in copies of the desired sequence of the nucleic acid flanked by the primers. The two different PCR primers are designed to anneal to opposite strands of the DNA at positions that allow the polymerase catalyzed extension product of one primer to serve as a template strand for the other, leading to the accumulation of a discrete double stranded fragment whose length is defined by the distance between the 5' ends of the oligonucleotide primers. Primer length can vary from about 10 to 50 or more nucleotides and are usually selected to be at least about 15 nucleotides to ensure high specificity. The double stranded fragment that is produced is called an "amplicon" and may vary in length from as few as about 30 nucleotides to 10,000 or more.

Chain extension of nucleic acids—extension of the 3'-end of a polynucleotide in which additional nucleotides or bases are appended. Chain extension relevant to the present invention is template dependent, that is, the appended nucleotides are determined by the sequence of a template nucleic acid to which the extending chain is hybridized. The chain extension product sequence that is produced is complementary to the template sequence. Usually, chain extension is enzyme catalyzed, preferably, in the present invention, by a thermophilic DNA polymerase.

Target nucleic acid sequence—a sequence of nucleotides to be studied either for the presence of a difference from a related sequence or for the determination of its presence or absence. The target nucleic acid sequence may be double stranded or single stranded and from a natural or synthetic source. When the target nucleic acid sequence is single stranded, the method of the present invention produces a nucleic acid duplex comprising the single stranded target nucleic acid sequence.

The target sequence usually exists within a portion or all of a nucleic acid, the identity of which is known to an extent sufficient to allow preparation of various primers necessary for introducing one or more priming sites flanking the target sequence or conducting an amplification of the target sequence or a chain extension of the products of such amplification in accordance with the present invention. Accordingly, other than for the sites to which the primers bind, the identity of the target nucleic acid sequence may or may not be known. In general, in PCR, primers hybridize to, and are extended along (chain extended), at least the target sequence, and, thus, the target sequence acts as a template. The target sequence usually contains from about 30 to 20,000 or more nucleotides, more frequently, 100 to 10,000 nucleotides, preferably, 50 to 1,000 nucleotides. The target nucleic acid sequence is generally a fraction of a larger molecule or it may be substantially the entire molecule. The minimum number of nucleotides in the target sequence is selected to assure that a determination of a difference between two related nucleic acid sequences in accordance with the present invention can be achieved.

Reference nucleic acid sequence—a nucleic acid sequence that is related to the target nucleic acid in that the two sequences are identical except for the presence of a difference, such as a mutation. Where a mutation is to be detected, the reference nucleic acid sequence usually contains the normal or "wild type" sequence. In certain situations the reference nucleic acid sequence may be part of the sample as, for example, in samples from tumors, the identification of partially mutated microorganisms, or identification of heterozygous carriers of a mutation. Consequently, both the reference and the target nucleic acid sequences are subjected to similar or the same amplification conditions. As with the target nucleic acid sequence, the identity of the reference nucleic acid sequence need be known only to an extent sufficient to allow preparation of various primers necessary for introducing one or more priming sites flanking the reference sequence or conducting an amplification of the target sequence or a chain extension of the products of such amplification in accordance with the present invention. Accordingly, other than for the sites to which the primers bind, the identity of the reference nucleic acid sequence may or may not be known. The reference nucleic acid sequence may be a reagent employed in the methods in accordance with the present invention. This is particularly the situation where the present method is used in PCR amplification for detection of a target nucleic acid sequence. Depending on the method of preparation of this reagent it may or may not be necessary to know the identity of the reference nucleic acid. The reference nucleic acid reagent may be obtained form a natural source or prepared by known methods such as those described below in the definition of oligonucleotides.

Holliday junction—the branch point in a four way junction in a complex of two identical nucleic acid sequences and their complementary sequences. The junction is capable of undergoing branch migration resulting in dissociation of the complex into two double stranded sequences where sequence identity and complementarity extend to the ends of the strands.

Complex—a complex of four nucleic acid strands containing a Holliday junction, which is inhibited from dissociation into two double stranded sequences because of a difference in the sequences and their complements. Accordingly, the complex is quadramolecular.

Related nucleic acid sequences—two nucleic acid sequences are related when they contain at least 15 nucleotides at each end that are identical but have different lengths or have intervening sequences that differ by at least one nucleotide. Frequently, related nucleic acid sequences differ from each other by a single nucleotide. Such difference is referred to herein as the "difference between two related nucleic acid sequences." A difference can be produced by the substitution, deletion or insertion of any single nucleotide or a series of nucleotides within a sequence.

Mutation—a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions and frameshift mutations. The latter entail the insertion or deletion of one to several nucleotide pairs. A difference of one nucleotide can be significant as to phenotypic normality or abnormality as in the case of, for example, sickle cell anemia. For the purposes of this application, a mutation may include a polymorphism.

Polymorphism—a difference in DNA sequence among individuals. For the purposes of this application, mutation as defined herein may represent a polymorphism. A single nucleotide polymorphism is a difference of one base pair between DNA sequences.

Partial duplex—a fully complementary double stranded nucleic acid sequence wherein one end thereof has non-complementary oligonucleotide sequences, one linked to each strand of the double stranded molecule, each non-complementary sequence having 8 to 60, preferably, 10 to 50, more preferably, 15 to 40, nucleotides. Thus, the partial duplex is said to be "tailed" because each strand of the duplex has a single stranded oligonucleotide chain linked thereto.

Duplex—a double stranded nucleic acid sequence wherein all of the nucleotides therein are substantially complementary.

Oligonucleotide—a single stranded polynucleotide, usually a synthetic polynucleotide. The oligonucleotide(s) are usually comprised of a sequence of 10 to 100 nucleotides, preferably, 20 to 80 nucleotides, and more preferably, 30 to 60 nucleotides in length.

Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol*, 101:20–78.

Other methods of oligonucleotide synthesis include phosphotriester and phosphodiester methods (Narang, et al. (1979) *Meth. Enzymol* 68:90) and synthesis on a support (Beaucage, et al. (1981) *Tetrahedron Letters* 22:1859–1862) as well as phosphoramidate technique, Caruthers, M. H., et al., *Methods in Enzymology,* 154:287–314 (1988), and others described in "Synthesis and Applications of DNA and RNA," S. A. Narang, editor, Academic Press, New York, 1987, and the references contained therein.

Oligonucleotide primer(s)—an oligonucleotide that is usually employed in a chain extension on a polynucleotide template such as in, for example, an amplification of a nucleic acid. The oligonucleotide primer is usually a synthetic oligonucleotide that is single stranded, containing a hybridizable sequence at its 3'-end that is capable of hybridizing with a defined sequence of the target or reference polynucleotide. Normally, the hybridizable sequence of the oligonucleotide primer has at least 90%, preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the hybridizable sequence of the oligonucleotide primer will be at least ten nucleotides, preferably at least 15 nucleotides and, preferably 20 to 50, nucleotides. In addition, the primer may have a sequence at its 5'-end that does not hybridize to the target or reference polynucleotides that can have 1 to 60 nucleotides, preferably, 8 to 30 polynucleotides.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases comprise adenine(A), guanine (G), inosine (I), and derivatives and analogs thereof. The pyrimidine bases comprise cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

Nucleotide—a base-sugar-phosphate combination that is the monomeric unit of nucleic acid polymers, i.e., DNA and RNA.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, and reverse transcriptase, and are preferably thermally stable DNA polymerases such as Vent® DNA polymerase, VentR® DNA polymerase, Pfu® DNA polymerase, Pfu Turbo® polymerase, Taq® DNA polymerase, and the like, derived from any source such as cells, bacteria, such as *E. coli,* plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Subcombination and remaining agents can then be combined and can be subjected to the present method.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Copy—means a sequence that is a direct identical copy of a single stranded polynucleotide sequence as differentiated from a sequence that is complementary to the sequence of such single stranded polynucleotide.

Conditions for extending a primer—includes a nucleotide polymerase, nucleoside triphosphates or analogs thereof capable of acting as substrates for the polymerase and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormone-hormone receptor, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring and synthetic receptors, e.g., thyroxine binding globulin, antibodies, enzymes, Fab fragments, lectins, nucleic acids, repressors, oligonucleotides, protein A, complement component C1q, or DNA binding proteins and the like.

Small organic molecule—a compound of molecular weight less than about 1500, preferably 100 to 1000, more preferably 300 to 600 such as biotin, digoxin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label—a member of a signal producing system. Labels include reporter molecules that can be detected directly by virtue of generating a signal, and specific binding pair members that may be detected indirectly by subsequent binding to a cognate that contains a reporter molecule such as oligonucleotide sequences that can serve to bind a complementary sequence or a specific DNA binding protein; organic molecules such as biotin or digoxigenin that can bind respectively to streptavidin and antidigoxin antibodies, respectively; polypeptides; polysaccharides; and the like. In general, any reporter molecule that is detectable can be used. The reporter molecule can be isotopic or nonisotopic, usually non-isotopic, and can be a catalyst, such as an enzyme, dye, fluorescent molecule, chemiluminescer, coenzyme, enzyme substrate, radioactive group, a particle such as latex or carbon particle, metal sol, crystallite, liposome, cell, etc., which may or may not be further labeled with a dye, catalyst or other detectable group, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label is a member of a signal producing system and can generate a detectable signal either alone or together with other members of the signal producing system. As mentioned above, a reporter molecule can serve as a label and can be bound directly to a nucleotide sequence. Alternatively, the reporter molecule can bind to a nucleotide sequence by being bound to an sbp member complementary to an sbp member that comprises a label bound to a nucleotide sequence. Examples of particular labels or reporter molecules and their detection can be found in U.S. Pat. No. 5,595,891, the relevant disclosure of which is incorporated herein by reference.

Signal Producing System—the signal producing system may have one or more components, at least one component being the label. The signal producing system generates a signal that relates to the presence of a difference between the target polynucleotide sequence and the reference polynucleotide sequence. The signal producing system includes all of the reagents required to produce a measurable signal. When a reporter molecule is not conjugated to a nucleotide sequence, the reporter molecule is normally bound to an sbp member complementary to an sbp member that is bound to or part of a nucleotide sequence. Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, enzymes and catalysts, and the like. The signal producing system provides a signal detectable by external means, such as by use of electromagnetic radiation, electrochemical detection, desirably by spectrophotometric detection. The signal-producing system is described more fully in U.S. Pat. No. 5,595,891, the relevant disclosure of which is incorporated herein by reference.

Ancillary Materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

Formation of Four Stranded Cruciform Structures

As mentioned above, one aspect of the present invention concerns a method for detecting the presence of a difference between two related nucleic acid sequences (a reference sequence and a target sequence). In the method, if there is a difference between the two related nucleic acid sequences, a stable quadramolecular complex is formed comprising both of the nucleic acid sequences in double stranded form. Usually, the complex comprises a Holliday junction. Both members of at least one pair of non-complementary strands within the complex have labels. The association of the labels as part of the complex is determined as an indication of the presence of the difference between the two related sequences. The method may be employed for detecting the presence of a mutation in a target nucleic acid sequence or for detecting the presence of a target nucleic acid sequence.

Figure 1B:
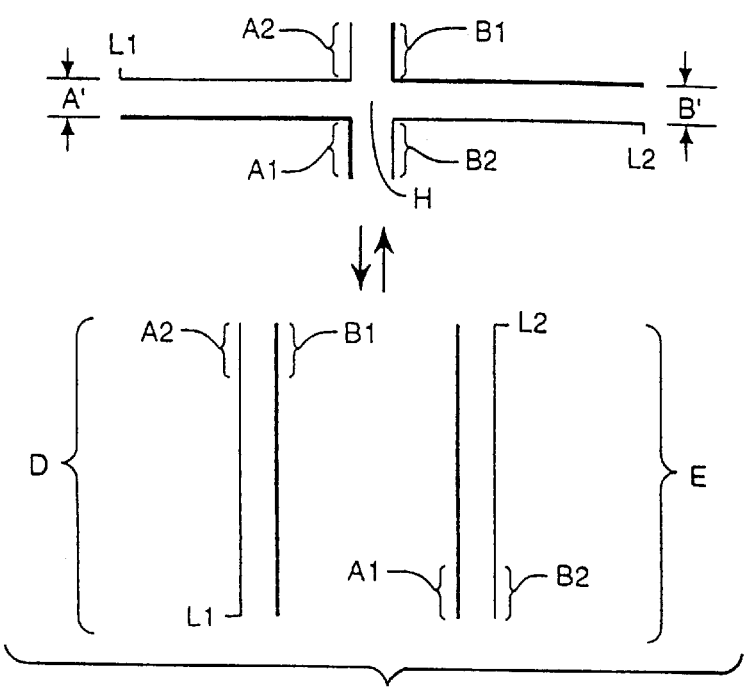

One aspect of the invention is depicted in FIG. 1A. Quadramolecular complex C comprises partial duplex A' and partial duplex B'. Partial duplexes A' and B' are related in that their hybridized portions are identical except for mutation M in partial duplex A'. Additionally, partial duplex A' has a label L1, which may or may not differ from label L2 in partial duplex B'. Oligonucleotide tail A1 of partial duplex A' is hybridized to corresponding oligonucleotide tail B2 of partial duplex B' and, similarly, oligonucleotide tail A2 of partial duplex A' is hybridized to oligonucleotide tail B1 of partial duplex B'. Accordingly, complex C is quadramolecular and contains a four way junction H. Because oligonucleotide tails A1 and B1 are different, branch migration can only proceed away from these tails and then only until mutation M is reached, at which point branch migration stops. Thus, as shown in FIG. 1A, when a mutation is present, complex C is stable and can be detected by determining whether both labels L1 and L2 have become associated. The association of the labels indicates the presence of complex C and thus the presence of mutation M in the target nucleic acid sequence. As shown in FIG. 1B, if mutation M is not present, branch migration continues until complete strand exchange occurs and only separate duplexes D and E are present whereupon no complex C is detected.

Figures 2A, 2B:
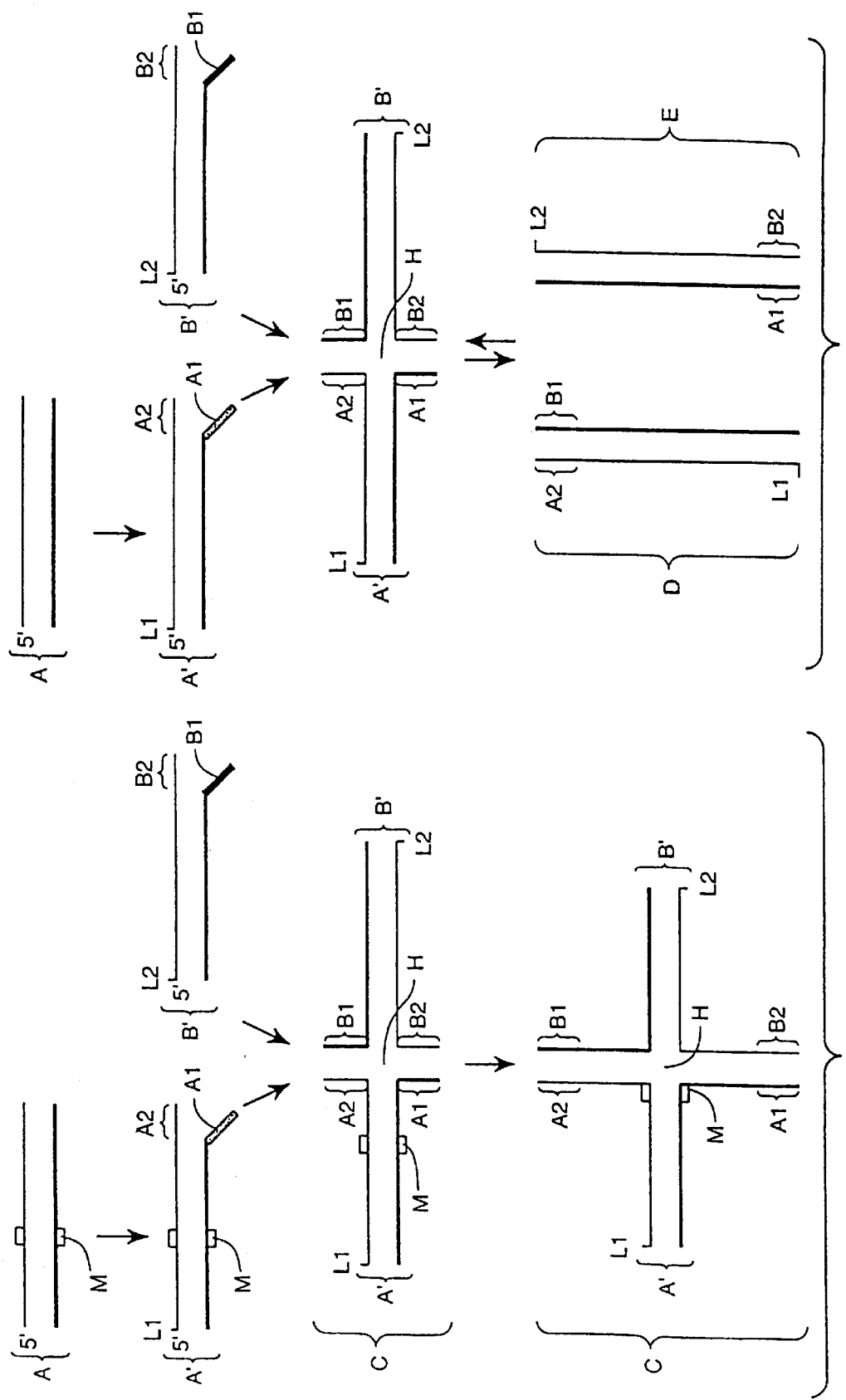
FIGS. 2A and 2B are schematic diagrams depicting the formation of the quadramolecular complex of the present invention from the tailed partial duplexes of the present invention.

Another embodiment in accordance with the present invention is depicted in FIGS. 2A and 2B. The method is for detecting a mutation within a target nucleic acid sequence A that contains mutation M. The method comprises forming from the target sequence a tailed target partial duplex A' comprised of a duplex of the target sequence, a label L1 and, at one end of the duplex, two non-complementary oligonucleotides A1 and A2, one linked to each strand of duplex A'. Oligonucleotides A1 and A2 have from 8 to 60 nucleotides, preferably, 15 to 30 nucleotides. The tailed target partial duplex is provided in combination with a labeled tailed reference partial duplex B' lacking mutation M. The tailed reference partial duplex B' is comprised of two nucleic acid strands that are identical to the strands in A' but for mutation M. Accordingly, one terminus of the tailed reference partial duplex B' has, as the end part of each strand, a sequence of non-complementary nucleotides B1 and B2, that are complementary to A2 and A1, respectively. Labels L1 and L2 are present in non-complementary strands of the tailed target and tailed reference partial duplexes (A' and B'). L1 and L2 may be the same or different.

Still referring to FIG. 2A, a complex C is formed as described above for FIG. 1A. Oligonucleotide tail A1 of A' is hybridized to corresponding oligonucleotide tail B2 of B' and, similarly, oligonucleotide tail A2 of A' is hybridized to oligonucleotide tail B1 of B'. Because oligonucleotide tails A1 and B1 are different, branch migration can only proceed away form these tails and then only until mutation M is reached, at which point branch migration stops. Thus, when a mutation is present, complex C is stable and can be detected by determining whether both labels L1 and L2 have become associated. The association of the labels indicates the presence of complex C. The formation of complex C is directly related to the presence of the mutation. Referring now to FIG. 2B, if mutation M is not present in the target nucleic acid A, branch migration in the complex continues until complete strand exchange has occurred and only the separate duplexes D and E are present. In this event no complex C is detected.

Production of Tailed Target Partial Duplexes by PCR and Chain Extension

Amplification of the Target Sequence by Polymerase Chain Reaction.

Figure 3:
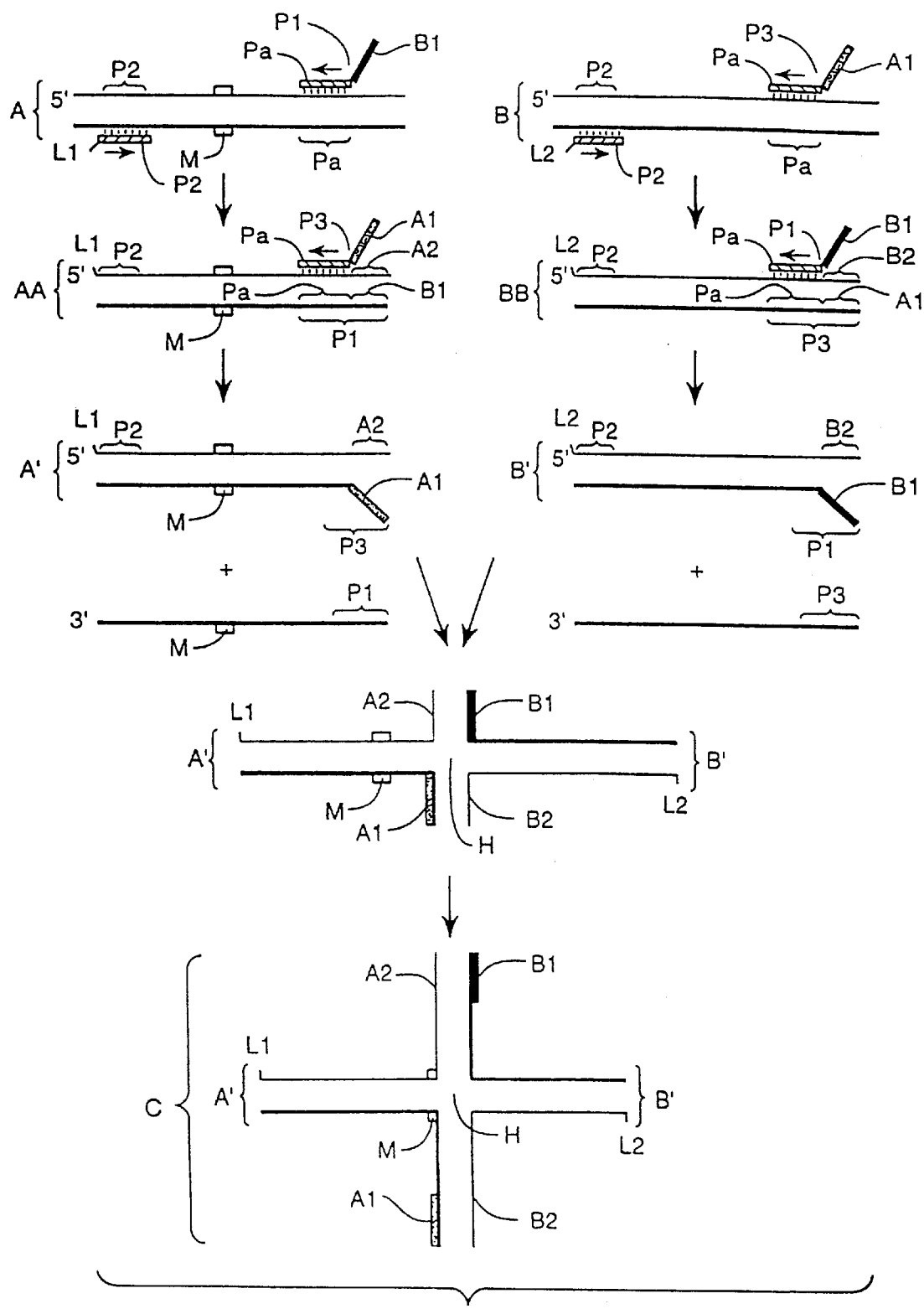
FIG. 3 is a schematic diagram depicting the production of the tailed partial duplexes of the present invention using one embodiment of a primer scheme of the present invention.

Another aspect of the present invention is shown in FIG. 3, which depicts, by way of example and not limitation, the production of tailed target partial duplex A' from target nucleic acid duplex A having mutation M, and the production of tailed reference partial duplex B' from reference nucleic acid duplex B. In the embodiment of FIG. 3, A is amplified by the polymerase chain reaction using primers P1 and P2 to produce an amplicon AA. Primer P2 contains a label L1 and primer P1 is comprised of a 3'-end portion Pa that can hybridize with the target sequence and 5'-end portion B1 that cannot hybridize with the target sequence. The amplification is carried out in the presence of a nucleotide polymerase and nucleoside triphosphates using temperature cycling. Amplicon AA has two strands, a labeled strand derived from primer P2 and an unlabeled strand derived from primer P1. The unlabeled strand has a 5'-end portion B1 of primer P1 and the labeled strand has a corresponding 3'-end portion A2, which is the complement of B1.

Chain Extension of Amplicon AA (Target Sequence)

Referring again to FIG. 3, a chain extension of primer P3 along the labeled strand of amplicon AA is then carried out to produce tailed target partial duplex A'. Primer P3 is comprised of a 3'-end portion Pa, which is identical to Pa of primer P1 and which binds to the labeled strand of AA. P3 has 5'-end portion A1 that is not complementary to amplicon AA. The chain extension is carried out in the presence of a nucleotide polymerase and nucleoside triphosphates under appropriate temperature conditions so that only the complementary strand of the labeled strand is produced and not a copy. In this particular embodiment this is achieved by removing primers P2 and P1 prior to extension of P3 in a manner as described hereinbelow. The complementary unlabeled strand of tailed target partial duplex A' has a 5'-end portion A1, which is not complementary to the 3'-end portion A2 of the labeled strand of A'. Unless the PCR reaction is carried out to produce an excess of the labeled strand, there will also be present the unlabeled strand from the amplification. This strand is not a template during chain extension to form partial duplex A'.

Amplification and Chain Extension of the Reference Sequence

In the embodiment of FIG. 3, reference nucleic acid sequence B is in a separate medium; primer P2 and primer P3 are employed in a polymerase chain reaction to produce amplicon BB. The amplification is carried out using temperature cycling under the conditions described below in the presence of a nucleotide polymerase and nucleoside triphosphates. B is comprised of a sequence identical to A except for mutation M. Generally, primer P2 used for this amplification contains a label L2 that may be the same as or different than L1. Amplicon BB has two strands, a labeled strand derived from primer P2 and an unlabeled strand derived from primer P3. The unlabeled strand has end portion A1 of primer P3 and the labeled strand has corresponding end portion B2, which is the complement of A1.

A chain extension of primer P1 along the labeled strand of amplicon BB is carried out, under the conditions mentioned above for the chain extension of primer P3 along the labeled strand in duplex AA, to produce tailed reference partial duplex B'. As mentioned above, primer P1 is comprised of portion Pa, which binds to the labeled strand of BB and portion B1 that does not bind to amplicon BB. The chain extension is carried out in the presence of a nucleotide polymerase and nucleoside triphosphates under appropriate temperature conditions so that only the complement of the labeled strand is produced and not a copy. The extended primer P1 has a 5'-end portion B1, which is not complementary to end portion B2 of the labeled strand of B'. As can be seen, A' and B' are related in that each of their labeled strands is complementary, except for mutation M, to the unlabeled strand of the other.

Reaction Conditions for PCR and Chain Extension

The above amplification is carried out by polymerase chain reaction utilizing temperature cycling to achieve denaturation of duplexes, oligonucleotide primer annealing, and primer extension by thermophilic template dependent nucleotide polymerase. In conducting PCR amplification of nucleic acids, the medium is cycled between two to three temperatures. The temperatures for the present method for the amplification by PCR generally range from about 50° C. to 100° C., more usually, from about 60° C. to 95° C. Relatively low temperatures of from about 50° C. to 80° C. are employed for the hybridization steps, while denaturation is carried out at a temperature of from about 80° C. to 100° C. and extension is carried out at a temperature of from about 70° C. to 80° C., usually about 72° C. to 74° C. The amplification is conducted for a time sufficient to achieve a desired number of copies for an accurate determination of whether or not two related nucleic acids have a difference. Generally, the time period for conducting the method is from about 10 seconds to 10 minutes per cycle and any number of cycles can be used from 1 to as high as 60 or more, usually 10 to 50, frequently, 20 to 45. As a matter of convenience it is usually desirable to minimize the time period and the number of cycles. In general, the time period for a given degree of amplification can be minimized, for example, by selecting concentrations of nucleoside triphosphates sufficient to saturate the polynucleotide polymerase, by increasing the concentrations of polynucleotide polymerase and polynucleotide primer, and by using a reaction container that provides for rapid thermal equilibration. Generally, the time period for conducting the amplification in the method of the invention is from about 5 to 200 minutes.

In an example of a typical temperature cycling as may be employed, the medium is subjected to multiple temperature cycles of heating at 90° C. to 100° C. for 2 seconds to 3 minutes and cooling to 65° C. to 80° C. for a period of 10 seconds to 3 minutes.

The conditions for carrying out the chain extension in accordance with the present invention are similar to those for the amplification described above. In general, the medium is heated to a temperature of 90° C. to 100° C. for a period of 2 to 500 seconds and then cooled to 20° C. to 80° C. for a period of 5 to 2000 seconds followed by heating to 40° C. to 80° C. for a period of 5 to 2000 seconds. Preferably, the medium is subjected to heating at 90° C. to 100° C. for a period of 10 seconds to 3 minutes, cooling to 50° C. to 65° C. for a period of 10 seconds to 2 minutes and heating to 70° C. to 80° C. for a period of 30 seconds to 5 minutes.

In carrying out the present method, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8, usually about 8 (at room temperature). In general for amplification, the pH and temperature are chosen and varied, as the case may be, so as to cause, either simultaneously or sequentially, dissociation of any internally hybridized sequences, hybridization of the oligonucleotide primer with the target nucleic acid sequence, extension of the primer, and dissociation of the extended primer. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The buffer employed in the present methods normally contains magnesium ion ($Mg^{2+}$), which is commonly used with many known polymerases, although other metal ions such as manganese have also been used. Preferably, magnesium ion is used at a concentration of from about 1 to 20 mM, preferably, from about 1.5 to 10 mM, more preferably, 2–4 mM. The magnesium can be provided as a salt, for example, magnesium chloride and the like. The primary consideration is that the metal ion permit the distinction between different nucleic acids in accordance with the present invention.

The concentration of the nucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The amount of the target nucleic acid sequences that is to be examined in accordance with the present invention can be as low as one or two molecules in a sample. The priming specificity of the primers used for the detection of a difference between two related nucleic acids and other factors will be considered with regard to the need to conduct an initial amplification of the target nucleic acid. It is within the purview of the present invention for detection of a mutation to carry out a preliminary amplification reaction to increase, by a factor of $10^2$ or more, the number of molecules of the target nucleic acid sequence. The amplification can be by any convenient method such as PCR, amplification by single primer, NASBA, and so forth, but will preferably be by PCR as described below.

The amount of the target nucleic acid sequence to be subjected to subsequent amplification using primers in accordance with the present invention may vary from about 1 to $10^{10}$, more usually from about $10^3$ to $10^8$ molecules, preferably at least $10^{-21}$M in the medium and may be $10^{-10}$ to $10^{-19}$M, more usually $10^{-14}$ to $10^{-19}$M.

If an initial amplification of the target nucleic acid sequence is carried to increase the number of molecules, it may be desirable, but not necessary, to remove, destroy or inactivate the primers used in the initial amplification depending on the nature of the protocol utilized. Accordingly, when the present method is carried out using step-wise addition of reagents for each separate reaction, such as, for example, in the embodiment of FIG. 3, primer P1 should be removed prior to the extension of primer P3. On the other hand, for example, in the embodiment described hereinbelow where the reactions are carried out simultaneously, it is not necessary to remove any of the primers. An example, by way of illustration and not limitation, of an approach to destroy the primers is to employ an enzyme that can digest only single stranded DNA. For example, an enzyme may be employed that has both 5' to 3' and 3' to 5' exonuclease activities, such as, e.g., exo VII. The medium is incubated at a temperature and for a period of time sufficient to digest the primers. Usually, incubation at 20° C. to 40° C. for a period of 10 to 60 minutes is sufficient for an enzyme having the above activity. The medium is next treated to inactivate the enzyme, which can be accomplished, for example, by heating for a period of time sufficient to achieve inactivation. Inactivation of the enzyme can be realized usually upon heating the medium at 90° C. to 100° C. for 0.5 to 30 minutes. Other methods of removing the primers will be suggested to those skilled in the art. It has been found, however, that removal of such primers is not necessary in carrying out the methods of the invention.

The amount of the oligonucleotide primer(s) used in the amplification reaction in the present invention will be at least as great as the number of copies desired and will usually be $10^{-9}$ to $10^{-3}$M, preferably, $10^{-7}$ to $10^{-4}$M. Preferably, the concentration of the oligonucleotide primer(s) is substantially in excess over, preferably at least 100 times greater than, more preferably, at least 1000 times greater than, the concentration of the target nucleic acid sequence. The concentration of the nucleoside triphosphates in the medium can vary widely; preferably, these reagents are present in an excess amount for both amplification and chain extension. The nucleoside triphosphates are usually present in $10^{-6}$ to $10^{-2}$M, preferably $10^{-5}$ to $10^{-3}$M.

Complex Formation and Detection of Branch Migration Inhibition

As shown in FIG. 3, following chain extension, the strands of partial duplexes A' and B' are allowed to bind and undergo branch migration by combining the mixtures containing partial duplexes A' and B' and incubating the combination at a temperature of 30° C. to 75° C., preferably 60° C. to 70° C., for at least one minute, preferably, 20 to 120 minutes, wherein complex C is formed as described above for FIGS. 1 and 2. Oligonucleotide tail A1 of A' is hybridized to corresponding oligonucleotide tail B2 of B' and, similarly, oligonucleotide tail A2 of A' is hybridized to oligonucleotide tail B1 of B'. Branch migration within complex C continues under the above temperature conditions with separation of the complex into duplexes D and E unless a mutation M is present, whereupon branch migration and strand dissociation is inhibited. Complex C is then detected, the presence of which is directly related to the presence of mutation M.

In the embodiment depicted in FIG. 3, labels L1 and L2 are incorporated into the partial duplexes that comprise complex C and provide a means for detection of complex C. This is by way of illustration and not limitation and other convenient methods for detecting complex C may be employed, such as the use of a receptor for the complex. In this approach there is required only one label, L1 or L2, which comprises a sbp member or a reporter molecule. A receptor for the sbp member and a receptor that can bind to complex C by virtue of a feature other than L1 or L2 can both bind to complex C and provide a means for detection.

Homogeneous Amplification, Chain Extension, Complex Formation and Detection

In the embodiment of FIG. 3, the reactions are carried out independently to produce tailed partial duplexes A' and B', respectively. Then, the reaction mixtures can be combined to allow the respective strands of A' and B' to bind to one another to form complex C.

Surprisingly, however, it was discovered that the reactions of the present invention can be carried out in the same reaction medium and many or all of the reactions may be carried out simultaneously. This is a particularly attractive feature of the present invention. In this approach a combination is provided in a single medium. The combination comprises (i) a sample containing a target nucleic acid sequence suspected of having a mutation, (ii) a reference nucleic acid sequence, which may be added separately if it is not known to be present in the sample and which corresponds to the target nucleic acid lacking the mutation, which as explained above may be the wild type nucleic acid, (iii) a nucleotide polymerase, (iv) nucleoside triphosphates, and (v) primers P1, P2 and P3, wherein P2 may include primer P2 labeled with L1 and primer P2 labeled with L2, or P2 may be unlabeled and primers P1 and P3 may be labeled respectively with L1 and L2. The medium is then subjected to multiple temperature cycles of heating and cooling to simultaneously achieve all of the amplification and chain extension reactions described above for FIG. 3 except that in this embodiment there is no need to avoid making copies of any of the extended primers. Preferably, in this embodiment, each cycle includes heating the medium at 90° C. to 100° C. for 2 seconds to 3 minutes, cooling the medium to 60° C. to 70° C. for a period of 8 seconds to 3 minutes, and heating the medium at 70° C. to 75° C. for a period of 10 seconds to 3 minutes although different temperatures may be required depending on the lengths of the primer sequences. Following the above temperature cycling the medium is subjected to heating for a period of time sufficient to denature double stranded molecules, preferably, at 90° C. to 99° C. for 10 seconds to 2 minutes, and cooled to 40° C. to 80° C., preferably 60° C. to 70° C., and held at this temperature for at least one minute, preferably for 20 minutes to 2 hours.

Following cooling of the medium all possible partial and complete duplexes are formed that can form from 1) single strands that have any combination of reference or mutant sequences and 5'-ends A2 and B2, and 2) single strands having any combination of reference or mutant sequences and 5'-ends A1 or B1 wherein the strands may further be labeled with either L1 or L2 when L2 and L2 are different. Among the partial duplexes that are formed are the tailed partial duplexes A' and B', which can bind to each other to form complex C, which does not dissociate into duplexes D and E when a mutation is present. A determination of the presence of such a complex is then made to establish the presence of a mutation in the target nucleic acid sequence. When primers P1 and P3 are labeled instead of primer P2, the labels L1 and L2 in partial duplexes A' and B' are attached to tails A1 and B1, respectively, which still provides for detection of complex C when a mutation is present.

While all the steps of this determination are preferably carried out in the same medium as that used for the above reactions, some or all of the steps can be carried out wholly or partially sequentially in different media. Thus, for example, PCR amplification of target sequence A and reference sequence B, each using primers P1, P2 and P3, can be conducted in separate solutions. The solutions can then be combined, heated to 90° C. to 100° C. to denature strands and then incubated as before at 40° C. to 80° C. to permit formation of duplexes and complex C when a mutation is present. Detection of complex C can then be carried out directly in the combined solutions or by adding reagents required for detection or by separating the complex C, for example, on a solid surface, and detecting its presence on the surface.

Initial Amplification of Target or Reference Sequences

Figure 4:
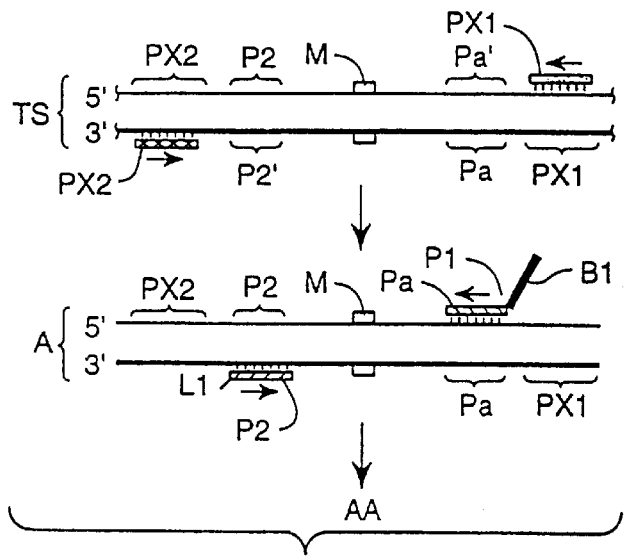
FIG. 4 is a schematic diagram depicting the production of the tailed target partial duplexes of the present invention using one embodiment of a primer scheme of the present invention following a pre-amplification of the target or reference sequence.

When a single reaction medium is used for detecting a difference between a target and reference nucleic acid, it may be necessary to conduct an initial amplification to increase the concentration of the target nucleic acid molecules and reference nucleic acid molecules relative to that of other nucleic acids that may be present in the sample. Referring now to FIG. 4., such initial amplification can be carried out using two additional primers PX1 and PX2 that bind to sites on the target and reference nucleic acids, which sites are upstream of the P2 binding site and the P1 and P3 binding site, respectively. This initial amplification can be carried out in the same medium as the above reactions. Thus, the target sequence TS, primers PX1, PX2, P1, P2 and P3 may all be combined with the target and reference sequences prior to temperature cycling as shown in FIG. 4. Two primers PX1 and PX2 are employed and bind to sites on TS that are upstream of the sites to which primers P1 and P2, respectively, bind. These sites are indicated by Pa' and P2', respectively, in FIG. 4. The sites to which primers PX1 and PX2 bind are generally within about 0 to 500 nucleotides, preferably, about 0 to 200 nucleotides away from Pa' and P2' and may overlap partially or completely with Pa' and P2'. PX1 and PX2 are extended along their respective strands. The amplification produces multiple copies of target nucleic acid sequence A. After appropriate denaturing, primers P1 and P2 are allowed to anneal to and extend along the respective strands of A to produce multiple copies of AA. The above also occurs for the reference DNA to produce multiple copies of reference nucleic acid B, which is further amplified with primers P2 and P3 to produce multiple copies of BB.

Preferably, when an initial amplification using primers PX1 and PX2 is carried out, these primers will be designed to anneal to the target and the reference nucleic acids at a higher temperature than that for primers P1, P2 and P3, respectively. This is usually achieved by selecting PX1 and PX2 sequences that are longer or more GC rich than P2 and the Pa binding sequence in P1 and P3. The initial amplification is then carried out at temperatures that exceed the temperature required for binding P1, P2 and P3 and the subsequent amplifications to form AA and BB are carried out at lower temperatures that permit P1, P2 and P3 to bind. It is then possible to detect the difference between target and reference nucleic acid sequences by combining the sequences, primers PX1, PX2, P1, P2 and P3 wherein P2 or P1 and P3 are labeled, polynucleotide polymerase, nucleotides triphosphates, and optionally the reagents needed to detect complex C, all in one medium. The initial amplification is carried out at temperatures that permit PX1 and PX2, but not P1, P2 and P3, to bind to the target sequence whereupon sequences A and B are formed. Temperature cycling is then carried out at a lower temperature where P1, P2 and P3 can bind and be extended. The mixture is then heated to 90° C. to 100° C. to denature the duplexes and cooled to permit formation of partial duplexes AA and BB and their hybridization to form complex C. The complex can then be detected directly if all of the necessary reagents are present or detection can be carried out in a separate step. The nature of primers PX1 and PX2, as well as the appropriate temperature for binding of these primers to the target sequence, are generally determined empirically with reference to the nucleotide composition of primers P1, P2 and P3.

The order of combining the various reagents may vary. The target nucleic acid may be combined with a preprepared combination of primers PX1, unlabeled P2, labeled P2, and P1 and P3, nucleoside triphosphates and nucleotide polymerase. Alternatively, the target nucleic acid, for example, can be combined with only primers PX1 and unlabeled P2 together with the nucleoside triphosphates and polymerase. After temperature cycling is carried out, the reaction mixture can be combined with the remaining primers P1 and labeled P2.

Introduction of P1, P2 and P3 Priming Sites on the Target and Reference Sequences In another approach in accordance with the present invention, priming sites for primers P1, P2 and P3 may be introduced to the target and reference sequences, usually flanking the target or reference sequence. A PCR step is employed utilizing adapter primers consisting of two regions: a 3'-proximal region which is hybridizable to a particular priming site on the target or reference nucleic acid sequence and a 5'-proximal region which is not hybridizable to the target or reference nucleic acid sequence and has substantially the same sequence as the 3'-proximal region of a primer used in amplifications described above employed in the detection of differences between two related nucleic acids. By "substantially the same sequence" is meant that an extension product produced in an amplification using the adapter primers contains a priming site to which such primer used in amplifications described above employed in the detection of differences between two related nucleic acids can hybridize. Such adapter primers are used to prepare target and reference nucleic acid sequences having specific, universal priming sites incorporated therein, which in turn are used as templates for a universal set of primers used in the amplifications described above in accordance with the present method for detection of differences between two related nucleic acid sequences.

Figure 5:
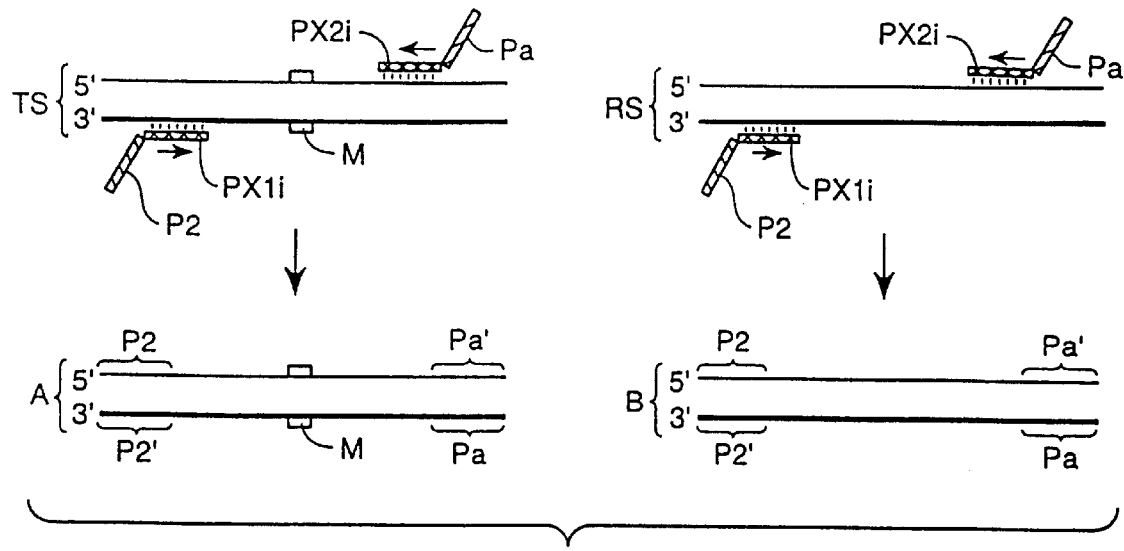
FIG. 5 is a schematic diagram a method of adding primer binding sites to the target or reference sequences.

Referring now to FIG. 5, an amplification is conducted, prior to amplifications to form AA and BB, using two additional primers PX1i and PX2i that bind to sites on the target and reference nucleic acids. This amplification may be carried out in the same or different reaction containers or different reaction media from that in which the amplifications to form AA and BB are carried out. For example, primers PX1i and PX2i are combined with the target and reference sequences, either in the same or different reaction medium, and subjected to temperature cycling. FIG. 5 shows an initial amplification for a mutant DNA analyte TS and a corresponding reference nucleic acid RS. Two primers PX1i and PX2i are employed and bind to respective priming sites on TS and RS. PX1i has a 3'-end portion that can hybridize with the target and reference sequence and 5'-end portion Pa that cannot hybridize with the target or reference sequence. PX2i has a 3'-end portion that can hybridize with the target and reference sequence and 5'-end portion P2 that cannot hybridize with the target or reference sequence. PX1i and PX2i are extended along their respective strands. The amplification produces multiple copies of extended primers that comprise the relevant portion of the target nucleic acid sequence and reference nucleic acid sequence flanked by priming sites Pa and P2, designated A and B, respectively.

The reaction products from this initial amplification are combined with primers P1, P2 and P3 as shown in FIG. 3. Primers P1 and P2 anneal to and extend along the respective strands of A to produce multiple copies of AA. The above also occurs for the reference DNA to produce multiple copies of reference nucleic acid B, which is further amplified with primers P2 and P3 to produce multiple copies of BB. The remainder of the reactions that occur are as described above to give A' and B', which then can form complex C.

The embodiment of FIG. 5 permits the use of universal primers P1, P2 and P3. This means that one set of primers for carrying out the reactions to produce complex C can be used for the analysis of a large number of target nucleic acid sequences and corresponding reference nucleic acid sequences. Such an approach involves the use of primers PX1i and PX2i, which are designed to introduce to the target and reference sequences priming sites for universal primers P1, P2 and P3. The relationship of PX1i and PX2i are such that each contains a 5'-end portion that corresponds to the priming sequence portion, i.e., the portion of the target sequence to which the primer hybridizes, at the 3'-end of primers P1, P2 or P3 as the case may be. In the embodiment shown in FIG. 5, PX1i contains 5'-end portion P2, which results in the introduction of priming site P2' in TS to which P2 can hybridize. Primer PX2i contains 5'-end portion Pa, which results in the introduction of priming site Pa' in TS to which Pa of primers P1 and P3 can hybridize.

It is within the purview of the present invention to utilize, in conjunction with the embodiment of FIG. 5, an initial amplification as described above and exemplified in FIG. 4 to increase the concentration of the target nucleic acid molecules and reference nucleic acid molecules relative to that of other nucleic acids that may be present in the sample.

The use of universal primers allows the methods in accordance with the present invention to be carried out less expensively in some applications than a method using a different set of such primers for each target nucleic acid sequence to be analyzed. The approach has particular application in searching large, continuous stretches (tens or hundreds of kilobases) of genomic DNA for a single meaningful sequence alteration that may or may not be present. Such areas include the comparison of DNA fragments in the neighborhood of a suspected gene in both healthy and affected individuals, development of polymorphic markers for the construction of high resolution genetic maps, research applications for correlation of particular phenotypes in various model organisms with specific DNA alterations, studies of diversity within a species, and so forth.

As mentioned above, the identity of the target nucleic acid sequence does not need to be known except to the extent to allow preparation of the necessary primers for carrying out the above reactions. The present invention permits the determination of the presence or absence of a mutation in a nucleic acid in a sample without the need to fully identify the sequence of the nucleic acid. Accordingly, one is able to determine the presence of a mutation in a nucleic acid between two sequences of nucleotides for which primers can be made.

Detection of the Quadramolecular Complex by Detecting the Association of the Labels In the present invention one means of detecting the quadramolecular complex involves the use of two labels on non-complementary strands. The labels become associated by virtue of both being present in the quadramolecular complex if a difference is present between the related sequences. Detection of the two labels in the complex provides for detection of the complex. Generally, the association of the labels within the complex is detected. This association may be detected in many ways. For example, one of the labels can be an sbp member and a complementary sbp member is provided attached to a support. Upon the binding of the complementary sbp members to one another, the complex becomes bound to the support and is separated from the reaction medium. The other label employed is a reporter molecule that is then detected on the support. The presence of the reporter molecule on the support indicates the presence of the complex on the support, which in turn indicates the presence of the mutation in the target nucleic acid sequence. An example of a system as described above is the enzyme-linked immunosorbent assay (ELISA), a description of which is found in "Enzyme-Immunoassay," Edward T. Maggio, editor, CRC Press, Inc., Boca Raton, Fla. (1980) wherein, for example, the sbp member is biotin, the complementary sbp member is streptavidin and the reporter molecule is an enzyme such as alkaline phosphatase.

Detection of the signal will depend upon the nature of the signal producing system utilized. If the reporter molecule is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the reporter molecule is a fluorescent molecule, the medium can be irradiated and the fluorescence determined. Where the label is a radioactive group, the medium can be counted to determine the radioactive count.

The association of the labels within the complex may also be determined by using labels that provide a signal only if the labels become part of the complex. This approach is particularly attractive when it is desired to conduct the present invention in a homogeneous manner. Such systems include enzyme channeling immunoassay, fluorescence energy transfer immunoassay, electrochemiluminescence assay, induced luminescence assay, latex agglutination and the like.

In one aspect of the present invention detection of the complex is accomplished by employing at least one suspendable particle as a support, which may be bound directly to a nucleic acid strand or may be bound to an sbp member that is complementary to an sbp member attached to a nucleic acid strand. Such a particle serves as a means of segregating the bound target polynucleotide sequence from the bulk solution, for example, by settling, electrophoretic separation or magnetic separation. A second label, which becomes part of the complex if a mutation is present, is a part of the signal producing system that is separated or concentrated in a small region of the solution to facilitate detection. Typical labels that may be used in this particular embodiment are fluorescent labels, particles containing a sensitizer and a chemiluminescent olefin (see U.S. Pat. No. 5,709,994, the disclosure of which is incorporated herein by reference), chemiluminescent and electroluminescent labels.

Preferably, the particle itself can serve as part of a signal producing system that can function without separation or segregation. The second label is also part of the signal producing system and can produce a signal in concert with the particle to provide a homogeneous assay detection method. A variety of combinations of labels can be used for this purpose. When all the reagents are added at the beginning of the reaction, the labels are limited to those that are stable to the elevated temperatures used for amplification, chain extension, and branch migration. In that regard it is desirable to employ as labels polynucleotides or polynucleotide analogs having 5 to 24 or more nucleotides depending on the nucleotides used and the nature of the analog. Polynucleotide analogs include structures such as polyribonucleotides, polynucleoside phosphonates, peptidonucleic acids, polynucleoside phosphorothioates, homo DNA and the like. In general, unchanged nucleic acid analogs provide stronger binding and shorter sequences can be used. Included in the reaction medium are oligonucleotide or polynucleotide analogs that have sequences of nucleotides that are complementary. One of these oligonucleotides or oligonucleotide analogs is attached to, for example, a reporter molecule or a particle. The other is attached to a primer, either primer P2 or primer P1 and/or P3 as a label. Neither the oligonucleotide nor polynucleotide analog should serve as a polynucleotide polymerase template. This is achieved by using either a polynucleotide analog or a polynucleotide that is connected to the primer by an abasic group. The abasic group comprises a chain of 1 to 20 or more atoms, preferably at least 6 atoms, more preferably, 6 to 12 atoms such as, for example, carbon, hydrogen, nitrogen, oxygen, sulfur, and phosphorus, which may be present as various groups such as polymethylenes, polymethylene ethers, hydroxylated polymethylenes, and so forth. The abasic group conveniently may be introduced into the primer during solid phase synthesis by standard methods.

Under the proper annealing temperature an oligonucleotide or polynucleotide analog attached to a reporter molecule or particle can bind to its complementary polynucleotide analog or oligonucleotide separated by an abasic site that has become incorporated into partial duplexes A' and B' as labels during amplification. If the partial duplexes become part of a quadramolecular complex, the reporter molecule or particle becomes part of the complex. By using different polynucleotide analogs or oligonucleotide sequences for labels, L1 and L2, two different reporter molecules or particles can become part of the complex. Various combinations of particles and reporter molecules can be used.

The particles, for example, may be simple latex particles or may be particles comprising a sensitizer, chemiluminescer, fluorescer, dye, and the like. Typical particle/reporter molecule pairs include a dye crystallite and a fluorescent label where binding causes fluorescence quenching or a tritiated reporter molecule and a particle containing a scintillator. Typical reporter molecule pairs include a fluorescent energy donor and a fluorescent acceptor dye. Typical particle pairs include (1) two latex particles, the association of which is detected by light scattering or turbidimetry, (2) one particle capable of absorbing light and a second label particle which fluoresces upon accepting energy from the first, and (3) one particle incorporating a sensitizer and a second particle incorporating a chemiluminescer as described for the induced luminescence immunoassay referred to in U.S. Pat. No. 5,340,716, which disclosure is incorporated herein by reference.

Briefly, detection of the quadramolecular complex using the induced luminescence assay as applied in the present invention involves employing a photosensitizer as part of one label and a chemiluminescent compound as part of the other label. If the complex is present the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed.

By way of illustration as applied to the present invention, a particle is employed, which comprises the chemiluminescent compound associated therewith such as by incorporation therein or attachment thereto. The particles have a recognition sequence, usually an oligonucleotide or polynucleotide analog, attached thereto with a complementary sequence incorporated into one of the nucleic acid strands as a label, L1. Another particle is employed that has the photosensitizer associated therewith. These particles have a recognition sequence attached thereto, which is different than that attached to the chemiluminescent particles. A complementary sequence is incorporated as a label L2 in the nucleic acid strand in complex C that is not complementary to the nucleic acid strand carrying label L1. Once the medium has been treated in accordance with the present invention to form a quadramolecular complex C, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the target polynucleotide having a mutation, the chemiluminescent compound is activated by the singlet oxygen and emits luminescence. The medium is then examined for the presence and/or the amount of luminescence or light emitted, the presence thereof being related to the presence of quadramolecular complex C. The presence of the latter indicates the presence and/or amount of the target polynucleotide having a mutation or of the target polynucleotide itself. Alternatively, by way of illustration as practiced in the present invention, the labels L1 and L2 may each comprise a ligand and the signal generating particles may each comprise a corresponding receptor each capable of binding L1 and L2, respectively.

Detection of a Target Sequence Using PCR

Figure 6A:
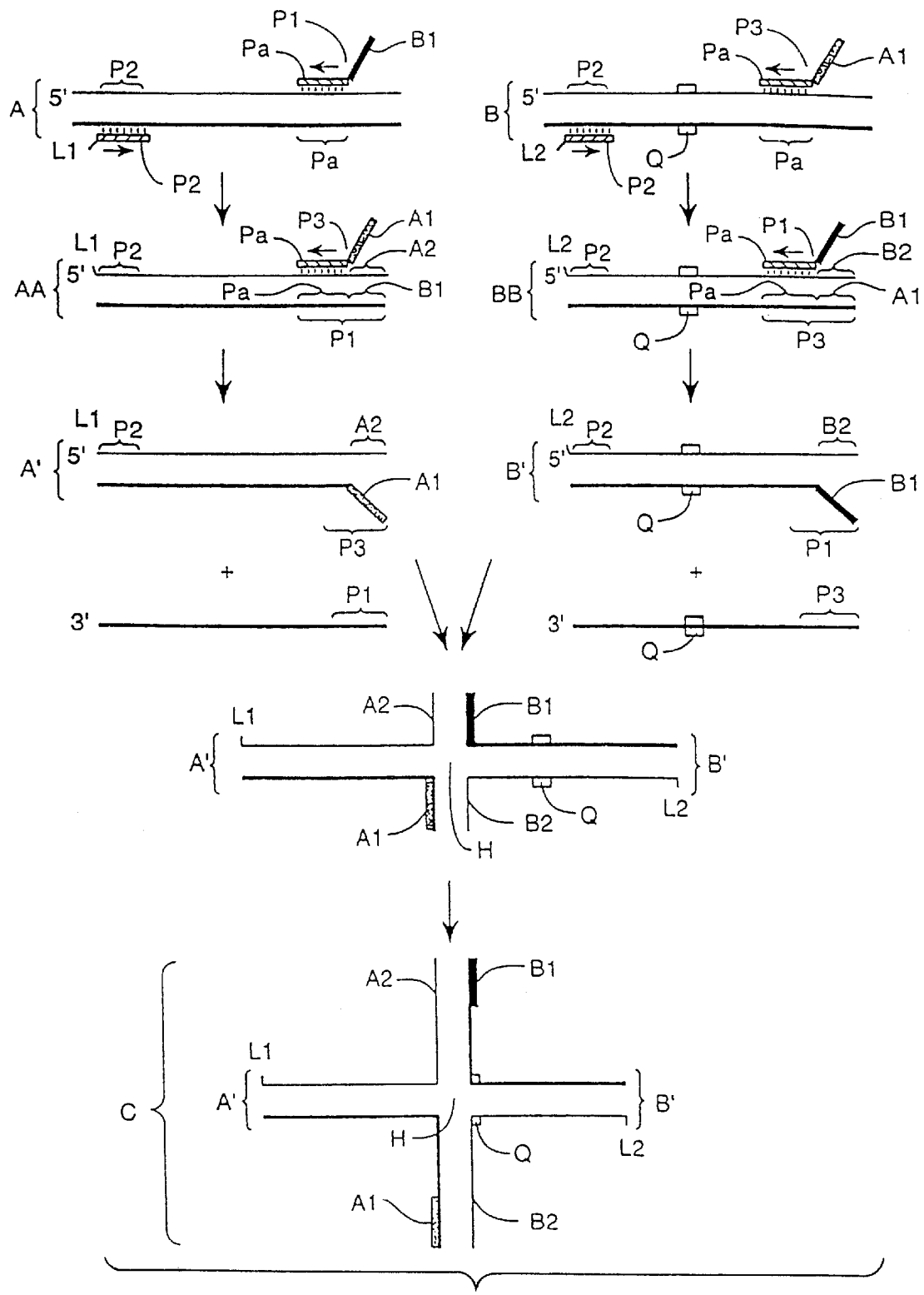
FIGS. 6A and 6B are schematic diagrams depicting the detection of a difference between a target nucleic acid sequence and a reference nucleic acid sequence using PCR.
Figure 6B:
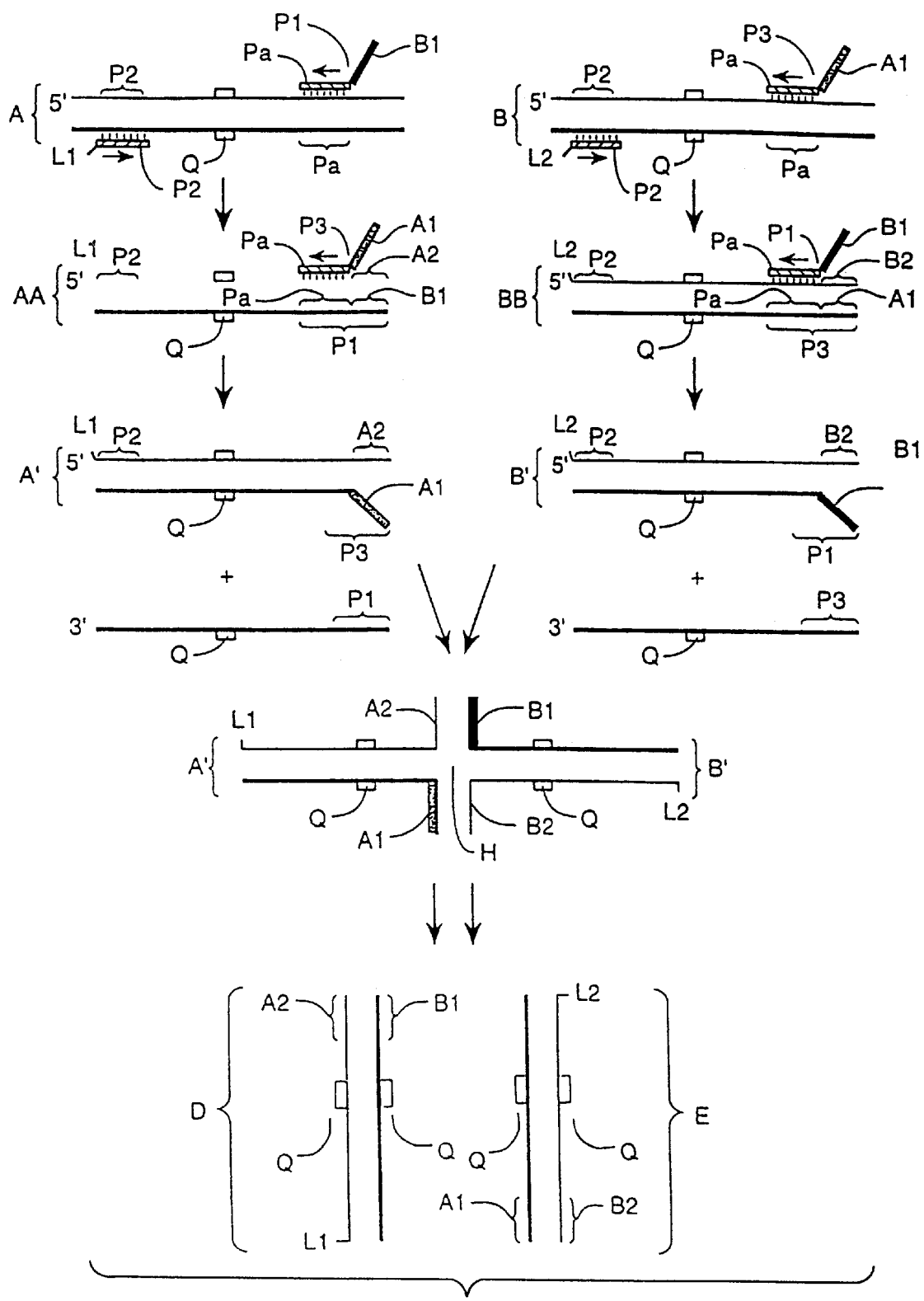

As mentioned above, the present invention also provides for detection of a target sequence using PCR. An example of this embodiment is depicted in FIGS. 6A and 6B. This PCR method involves formation of a four-strand structure or complex as above for the detection of a mutation. However, in the approach in FIGS. 6A and 6B, the target nucleic acid sequence A is the sequence to be detected by PCR and the reference nucleic acid sequence B is introduced as a reagent and contains a difference Q from the target nucleic acid sequence. This difference is as described above for two related nucleic acid sequences. Thus, in this embodiment the identity of the target nucleic acid sequence is known to the extent necessary to allow the preparation of the primers and the reference nucleic acid sequence. The formation of such complex involves producing two partial duplexes by amplification by using three different primers in the polymerase chain reaction and allowing the amplified products to anneal. In this particular embodiment the formation of the complex is dependent on the presence of the target nucleic acid sequence. If the target nucleic acid sequence is not present, no complex is detected. However, when the target nucleic acid is present, there is a difference between the two hybridized portions of the complex. The complex does not dissociate and can be detected to as an indication of the presence of the target nucleic acid sequence.

Referring now to FIGS. 6A and 6B, target nucleic acid A, if present, is amplified by the polymerase chain reaction using primers P1 and P2 to produce an amplicon AA. Primer P2 contains a label L1 and primer P1 is comprised of a 3'-end portion Pa that can hybridize with the target sequence and 5'-end portion B1 that cannot hybridize with the target sequence. The amplification is carried out under the reaction conditions employed in PCR in the presence of a nucleotide polymerase and nucleoside triphosphates using temperature cycling. Amplicon AA has two strands, a labeled strand derived from primer P2 and an unlabeled strand derived from primer P1. The unlabeled strand has a 5'-end portion B1 of primer P1 and the labeled strand has a corresponding 3'-end portion A2, which is the complement of B1.

A chain extension of primer P3 along the labeled strand of amplicon AA is then carried out to produce tailed target partial duplex A'. Primer P3 is comprised of a 3'-end portion Pa, which is identical to Pa of primer P1 and which binds to the labeled strand of AA. P3 has 5'-end portion A1 that is not complementary to amplicon AA. The chain extension is carried out in the presence of a nucleotide polymerase and nucleoside triphosphates under appropriate temperature conditions so that only the complementary strand of the labeled strand is produced and not a copy. This complementary unlabeled strand of tailed target partial duplex A' has a 5'-end portion A1, which is not complementary to the 3'-end portion A2 of the labeled strand of A'. Unless the PCR reaction is carried out to produce an excess of the labeled strand, there will also be present the unlabeled strand from the amplification. This strand is not a template during chain extension to form partial duplex A'.

In the embodiment of FIGS. 6A and 6B, reference nucleic acid sequence B is amplified in a separate medium, using primer P2 and primer P3, by polymerase chain reaction to produce amplicon BB. The amplification is carried out using temperature cycling under the conditions described above in the presence of a nucleotide polymerase and nucleoside triphosphates. B is comprised of a sequence identical to A except for difference Q. Generally, primer P2 used for this amplification contains a label L2 that may be the same as or different than L1. Amplicon BB has two strands, a labeled strand derived from primer P2 and an unlabeled strand derived from primer P3. The unlabeled strand has end portion A1 of primer P3 and the labeled strand has corresponding end portion B2, which is the complement of A1.

A chain extension of primer P1 along the labeled strand of amplicon BB is carried out, under the conditions mentioned above for the chain extension of primer P3 along the labeled strand in duplex AA, to produce tailed reference partial duplex B'. As mentioned above, primer P1 is comprised of portion Pa, which binds to the labeled strand of BB and portion B1 that does not bind to amplicon BB. The chain extension is carried out in the presence of a nucleotide polymerase and nucleoside triphosphates under appropriate temperature conditions so that only the complement of the labeled strand is produced and not a copy. The extended primer P1 has a 5'-end portion B1, which is not complementary to end portion B2 of the labeled strand of B'. As can be seen, A' and B' are related in that each of their labeled strands is complementary to the unlabeled strand of the other except for difference Q.

The strands of partial duplexes A' and B' are allowed to bind and undergo branch migration by combining the mixtures containing partial duplexes A' and B' and incubating the combination under conditions described above for mutation detection wherein complex C is formed if the target nucleic acid sequence is present. Oligonucleotide tail A1 of A' is hybridized to corresponding oligonucleotide tail B2 of B' and, similarly, oligonucleotide tail A2 of A' is hybridized to oligonucleotide tail B1 of B'. Branch migration within complex C continues until difference Q is reached, at which point migration ceases. In the embodiment depicted in FIG. 8, labels L1 and L2 are incorporated into the partial duplexes that comprise complex C.

In the embodiment of FIGS. 6A and 6B, the reactions are carried out independently to produce tailed partial duplexes A' and B', respectively. Then, the reaction mixtures can be combined to allow the respective strands of A' and B' to bind to one another to form complex C.

It is a particularly attractive feature of the present invention that the method for the use of PCR in the detection of a target nucleic acid sequence can be carried out in a single reaction container without a separation step. In this embodiment, a combination is provided in a single medium. The combination comprises (i) a sample suspected of containing a target nucleic acid sequence, (ii) a reference nucleic acid sequence, related to but different from the target nucleic acid sequence, (iii) a nucleotide polymerase, (iv) nucleoside triphosphates, and (v) primers P1, P2 and P3, wherein P2 may include primer P2 labeled with L1 and primer P2 labeled with L2, or P2 may be unlabeled and primers P1 and P3 may be labeled respectively with L1 and L2. The medium is then subjected to multiple temperature cycles of heating and cooling to simultaneously achieve all of the amplification and chain extension reactions described above for FIG. 8A except that in this embodiment there is no need to avoid making copies of any of the extended primers. The medium is subjected to conditions for conducting PCR as described above.

When target nucleic acid is present, all possible partial and complete duplexes are formed that can form from 1) single strands that have any combination of reference or target sequences and 5'-ends A2 and B2, and 2) single strands having any combination of reference or mutant sequences and 5'-ends A1 or B1 wherein the strands may further be labeled with either L1 or L2 when L1 and L2 are different. Among the partial duplexes that are formed are the tailed partial duplexes A' and B', which can bind to each other to form complex C, which does not dissociate. A determination of the presence of such a complex is then made to establish the presence of the target nucleic acid sequence. When primers P1 and P3 are labeled instead of primer P2, the labels L1 and L2 in partial duplexes A' and B' are attached to tails A1 and B1, respectively, which still provides for detection of complex C when target nucleic acid sequence is present.

When target nucleic acid sequence is not present (i.e. target is identical to reference, see FIG. 6B), two duplexes form by virtue of the amplification of the reference nucleic acid sequence wherein one can achieve an initial PCR amplification with both sets of primers, namely, P2 and P3 on the one hand (represented by duplex BB in FIG. 8B) and P2 and P1 on the other (represented by duplex BB in FIG. 8B). Chain extension of primer P1 on amplicon BB produces B', and chain extension primer P3 on amplicon bb produces b'. Any four strand structure formed by hybridization of the respective tails of B' and b' to one another completely dissociates because there is no difference in either of the duplexes to inhibit complete strand exchange. In other words, the complex dissociates into normal duplex structures D' and E' by strand exchange by means of branch migration when the hybridized portions of each partial duplex are identical. In this embodiment in the absence of target nucleic acid sequence, the hybridized portions are identical in that each strand contains difference Q.

Reduction of Background Signal by the Use of Alternative Primers (P4 and P5)

Another embodiment of the present invention includes a way of reducing the background due to false priming in PCR. In the homogeneous detection methods of the present invention, non-specific signals generated by various false priming products may add up to a substantial background. Methods to minimize false priming in PCR have been described previously, including among others, a standard wax mediated hot start procedure as described in Chou, Q., et al, Prevention of pre-PCR mis-priming and primer dimerization improves low-copy-number amplifications, *Nucleic Acids Res.* 20:1717–1723 (1992), and a procedure that utilizes 3'-etheno modified PCR primers, as described in PCT WO 98/28443. The present method of the invention provides means for reducing background signals due to false priming by rendering the products of false priming undetectable. This method can prevent formation of signal generating complexes due to mis-priming when more than one priming region is available on the target strands or reference strands.

As described above, PCR amplification of the target and reference sequences, using a combination of the primers of the present invention, produce labeled duplexes having predetermined tail sequences that are not complementary to the target or reference. Thus, all products produced by PCR amplification with these primers are capable of forming partial duplexes, which can further bind to each other by hybridization of the tail sequences to form four stranded DNA complexes. When the double stranded portions of the partial duplexes are different from each other by a mutation M, strand exchange in the four stranded DNA structures is prevented, resulting in the formation of a stable quadramolecular complex. In a similar manner, non-specific amplification products resulting from mis-priming become labeled and comprise tail sequences at one end. These products can form partial duplexes, which can further bind to partial duplexes produced by specific amplification, as well as to partial duplexes produced by non-specific amplification. Since the target-related double-stranded portions of the quadramolecular complex produced from the combination of partial duplexes produced by specific and non-specific priming are entirely different, such complexes cannot exchange strands and dissociate into labeled full duplexes. The stable quadramolecular complexes are detectable, and thus generate a signal that is related to non-specific priming but not to the presence of a mutation.

Figure 7:
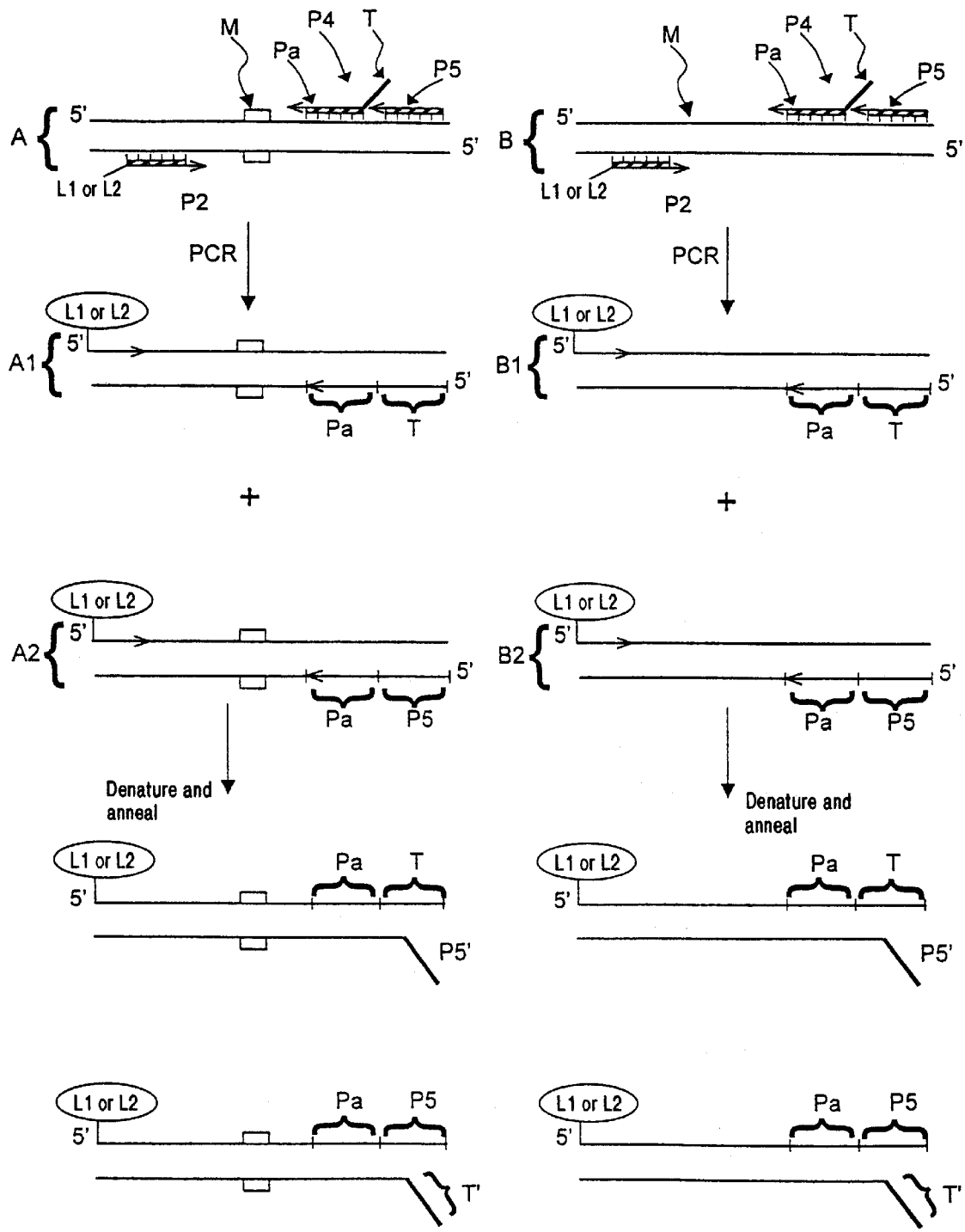
FIG. 7 is a schematic diagram representing a primer scheme of the present invention which reduces the effects of false priming in the amplification reaction of the present invention.

To prevent the signals resulting from mis-priming, one embodiment of the present invention uses an alternative design of the primers. Referring now to FIG. 7, primer P2

(labeled as previously described herein) binds to a first strand of the target sequence (A) having a mutation M and the reference sequence (B). Primers P4 and P5 are capable of binding to the second strand of the target A and the reference B. Primer P4 comprises a 3'-end Pa region that is complementary to the target or reference, and a 5'-end tail T that is not complementary to the target or reference. The Pa region of P4 binds to the second strand at a location upstream (in the 5'-direction) from sequence that binds P5. Although FIG. 7 shows Pa binding to the second strand immediately adjacent to P5, small gaps or partial overlaps between these two sequences are consistent with the present invention. The amount of gap or overlap can be determined experimentally (see examples) and the invention is not limited to any particular number of bases. Likewise, in FIG. 7 and the examples below, T and P5 have the same length but this is not required to practice the invention. It is desirable that the $T_m$ of T be close to the $T_m$ of P5.

Referring to FIG. 7, amplification of the target and reference sequences by PCR using primers P2, P4 and P5, under conditions previously described herein, produces duplexes comprising the target and reference sequences with either sequence T and its complement at one end (duplexes A1 and B1), or sequence P5 and its complement at one end (duplexes A2 and B2). Following denaturation and reannealing of the amplification mixture, the amplification products form tailed partial duplexes. The tailed partial duplexes comprise double stranded target and reference sequences having non-complementary single strands at the end of each strand of the duplex. The non-complementary single stranded sequences comprise T, its complementary sequence T', and P5 and its complement P5'.

Figure 8:
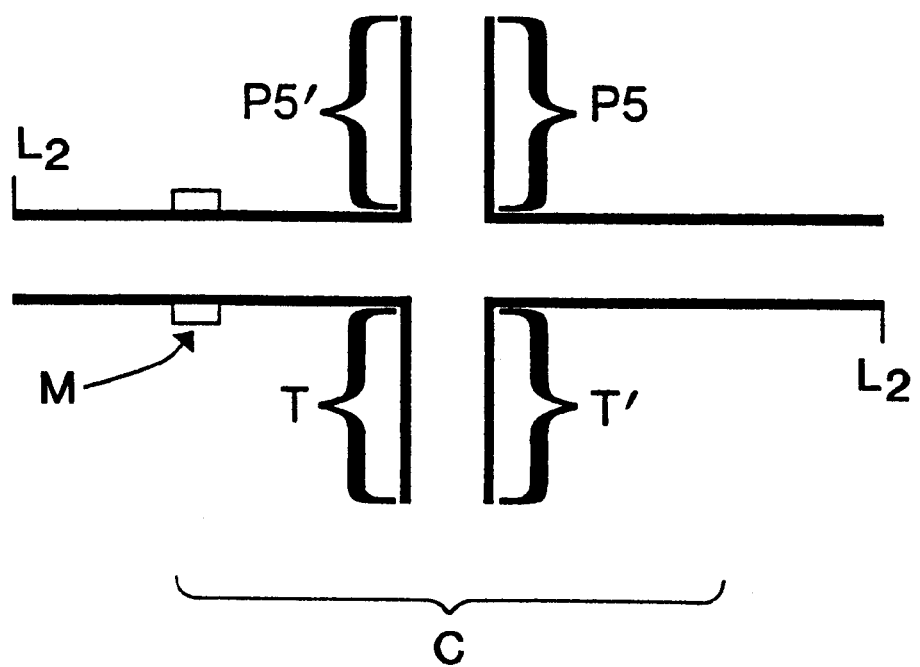
FIG. 8 is a schematic diagram of the quadramolecular complex of the present invention.

Referring to FIG. 8, the tailed partial duplexes bind to each other by hybridization of the corresponding tails to form a four-stranded DNA complex C. As shown in FIGS. 1A and 1B, branch migration within complex C results in separation of the complex into duplexes unless a mutation M is present, whereupon branch migration and strand dissociation is inhibited. Complex C is then detected due to the association of labels L1 and L2, the presence of which is directly related to the presence of mutation M.

Amplification of the target sequence and the reference sequence can be accomplished separately or, preferably, in the same reaction medium. This combination comprises (a) a sample containing a target nucleic acid sequence suspected of having a mutation, (b) a reference nucleic acid sequence, which may be added separately if it is not known to be present in the sample and which corresponds to the target nucleic acid lacking the mutation, which as explained above may be the wild type nucleic acid, (iii) a nucleotide polymerase, (iv) nucleoside triphosphates, and (v) primers P2, P4 and P5. Primer P2 may be labeled with L1 and separately labeled with L2, or primers P4 and P5 may be labeled respectively with L1 and L2. The medium is then subjected to multiple temperature cycles of heating and cooling to simultaneously achieve all of the amplification and chain extension reactions necessary. Preferably, in this embodiment, each cycle includes heating the medium at 90° C. to 100° C. for 2 seconds to 3 minutes, cooling the medium to 50° C. to 70° C. for a period of 8 seconds to 3 minutes, and heating the medium at 70° C. to 75° C. for a period of 10 seconds to 3 minutes although different temperatures may be required depending on the lengths of the primer sequences. Following the above temperature cycling the medium is subjected to heating for a period of time sufficient to denature double stranded molecules. The reaction mixture is then cooled to allow (1) the single stranded molecules to reanneal to form tailed partial duplexes, (2) the binding of the tailed partial duplexes to form four stranded complexes, and (3) the complexes to undergo strand exchange by branch migration. Preferably the medium is heated to 90° C. to 99° C. for 10 seconds to 2 minutes for denaturation, and then cooled to 40° C. to 80° C., preferably 60° C. to 70° C., and held at this temperature for at least one minute, preferably for 20 minutes to 2 hours, for reannealing and strand exchange.

Referring now to FIG. 8, among the partial duplexes formed following cooling of the medium are the tailed partial duplexes which can bind to each other to form complex C. As represented in in FIGS. 1A and 2A the complex does not dissociate into duplexes when a mutation is present (the partial duplexes of FIGS. 1A and 2A were generated using the primer scheme described for that embodiment; however, the principle of strand exchange in the complex is the same regardless of the primer scheme used to generate the partial duplexes.) A determination of the presence of such a complex is then made to establish the presence of a mutation in the target nucleic acid sequence. When primers P4 and P5 are labeled instead of primer P2, the labels L1 and L2 in the partial duplexes are attached to the non-complementary tails which still provides for detection of complex C when a mutation is present.

As previously described herein, branch migration within the four stranded DNA complexes continues unless a mutation M is present. See FIGS. 1 and 2. Labels as previously described can be incorporated into the partial duplexes and provide a means for detection of the four stranded complex. See FIGS. 3 and 8. If a mutation is present, the labels become associated by virtue of both being present in the complex. As previously described herein, detection of the labels provides for detection of the complex.

Both primers P4 and P5 can have false priming sites in the target and reference DNA, but it is highly unlikely that these sites are adjacent to each other. Thus, the respective non-specific PCR products would not share complementary target-related sequences and, therefore, cannot form partial duplexes which are capable of binding to each other to form the four stranded complex C. Consequently, non-specific PCR products resulting from non specific priming do not contribute to the signal related to the presence of a mutation in the target sequence.

When primers P4 and P5 are combined in the amplification mixture, the two primers may compete with each other. That is to say, the amplification product of primers P2 and P5 comprises sequence Pa and its complement which is a priming site for primer P4, whereas the amplification product of primer pair P2 and P4 does not contain a priming site for the primer P5. Thus, primer P4 can be extended along a strand of either one of the amplification products, while primer P5 can bind and be extended only along a strand of the product produced by amplification using primers P2 and P5. If primer P4 is as efficient or more efficient than primer P5, it is possible for primer P4 to outperform primer P5. Under these conditions, amplification of target or reference nucleic acid sequences will result in a single amplification product generated by primers P2 and P4, and subsequently result in inability to form partial duplexes. Hence, the balanced performance of primers P4 and P5 in a mixture should be considered, and may depend on the relative thermodynamic parameters for binding of each of these primers to the strand of the target and reference nucleic acid sequence. Ideally, to maximize the yield of signal-generating four-stranded structures, the amounts of the amplification products generated by P4 and P5 should be equal. The balanced priming efficiency of primers P4 and P5 can be achieved based on thermodynamic considerations or by optimization of the ratios of the concentration of the two primers as well as the temperature for annealing of the primers during the amplification procedure.

In a typical optimization experiment, several different ratios are examined at various PCR cycle annealing temperatures ($T_a$). The absolute value of signal measured in an induced luminescence assay (see U.S. Pat. No. 5,595,891) is a good criterion for optimizing the ratio of the concentrations of primers P4 and P5. As an example, the absence of a signal obtained when the target nucleic acid sequence is known to comprise a mutation (provided that amplification did not fail, as judged by gel electrophoresis) means that the priming efficiency of primer P4 used for the amplification of the target and reference nucleic acid sequence overwhelmed that of primer P5, resulting in the generation of only one amplification product and the subsequent inability to produce partial duplexes and the complex C. An example of such experiment is shown below.

Figure 9:
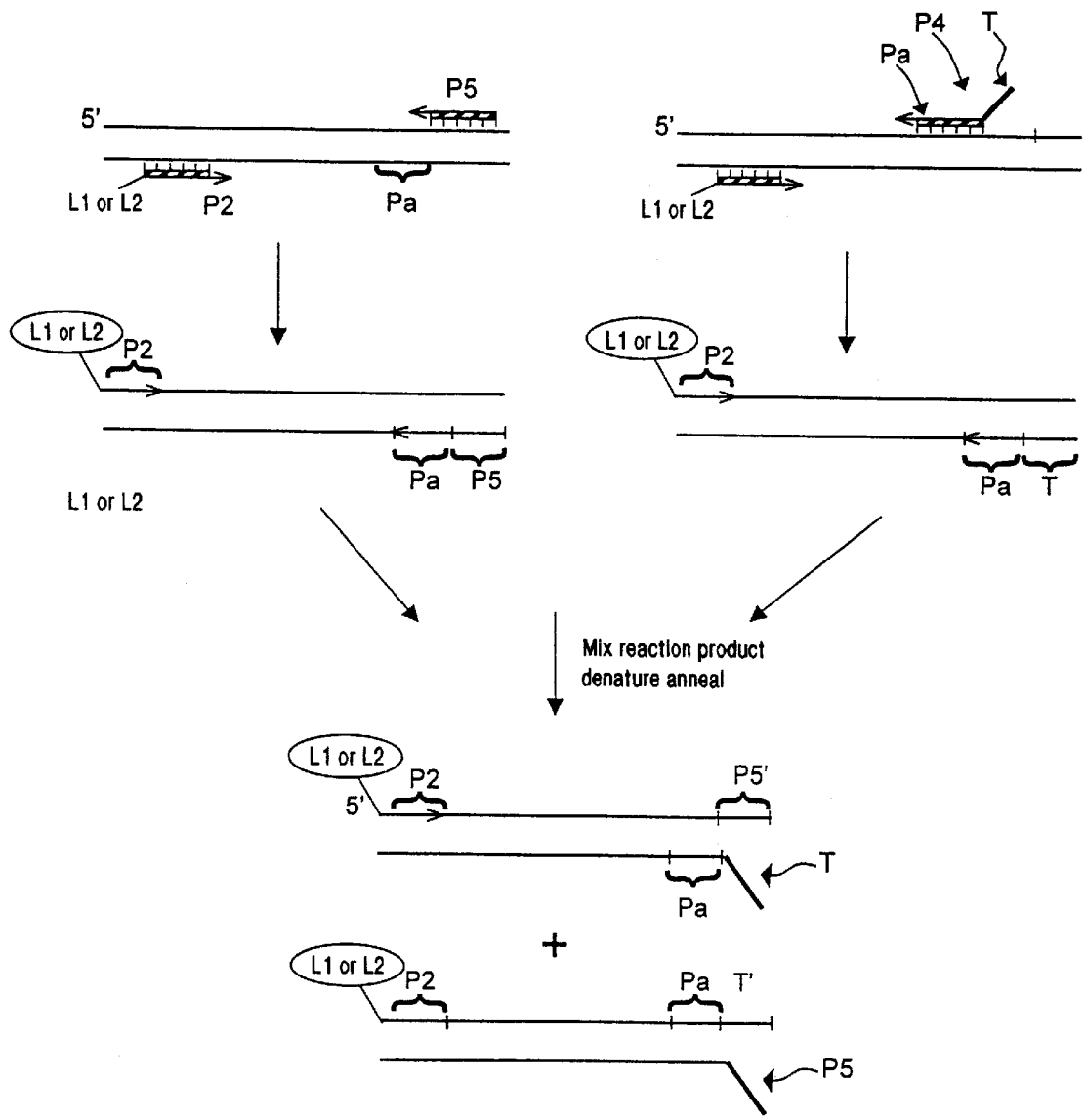
FIG. 9 is a schematic diagram depicting the amplification of the reference sequence the target sequence using the primers of the present invention.

Referring now to FIG. 9, the present invention can also be carried out by separate PCR amplification of target or reference nucleic acid sequences by combination of primers P2 and P4 in one reaction vessel, and combination of primers P2 and P5 in another reaction vessel. Following PCR amplification, the reaction mixtures are combined and the combination is further subjected to conditions leading to denaturation of the double-stranded products, annealing of the single strands, and formation of partial duplexes which bind to each other by hybridization of the tail sequences to form four-stranded DNA complexes C. This procedure eliminates the need for balanced priming efficiency of primers P4 and P5, as discussed above. Similarly, when primer P2 is labeled, it is possible to carry out the invention by amplifying the target nucleic acid sequence using primer P2 labeled with one of the labels, and separately amplifying the reference sequence using primer P2 labeled with the second label. Following PCR amplification, the reaction mixtures are combined and the combination is subjected to conditions leading to denaturation of the double-stranded products, annealing of the single strands to form partial duplexes and binding of the partial duplexes to each other by hybridization of the tail sequences to form four-stranded DNA complexes.

As mentioned above, it is within the purview of the present invention to utilize an initial amplification to increase the concentration of the target nucleic acid molecules and reference nucleic acid molecules relative to that of other nucleic acids that may be present in the sample. When using the alternative method of the invention, which is aimed at rendering non-specific amplification products undetectable, initial amplification of target and reference nucleic acid sequences can be carried out using the above mentioned primers PX1 and PX2. Alternatively, initial amplification can be carried out using primers PX1 and P2 or PX2 and P5. Following initial amplification of target and reference nucleic acid sequences, the reaction mixture is combined with primers P2, P4 and P5, as described above, and the combination is subjected to thermocycling conditions suitable for polymerase chain reaction and formation of partial duplexes. The partial duplexes produced from target and reference nucleic acid sequences are combined and allowed to hybridize to each other to form the four stranded DNA complexes. The formation of stable complex C is detected by the association of the labels as mentioned above. The detection of stable complex C is indicative of the presence of a mutation of sequence difference in the target nucleic acid sequence.

Kits for Practicing the Invention

As a matter of convenience, predetermined amounts of reagents employed in the present invention can be provided in a kit in packaged combination. A kit can comprise in packaged combination (a) a primer P2 that is extendable along one of the strands of the target and reference nucleic acid sequences, (b) a primer P1 comprising a 3'-end portion Pa that binds to and is extendable along the other of the strands of the target and reference nucleic acid sequences and a 5'-end portion B1 that does not bind to the target and reference nucleic acid sequences, and (c) a primer P3 comprising 3'-end portion Pa and a portion A1 that is different from B1 and does not bind to the target and reference nucleic acid sequences. Preferably, primer P2 can be labeled, but primers P1 and P3 alternatively may be labeled. The kit can also include a reference nucleic acid, which corresponds to a target nucleic acid sequence except for the possible presence of a difference such as a mutation, and reagents for conducting an amplification of target nucleic acid sequence prior to subjecting the target nucleic acid sequence to the methods of the present invention. The kit can also include nucleoside triphosphates and a nucleotide polymerase. The kit can further include two additional oligonucleotide primers PX1 and PX2 where the primers are related in that a product of the extension of one along the target sequence serves as a template for the extension of the other. The kit can further include particles as described above capable of binding to the label on at least one of the primers. The kit can further include members of a signal producing system and also various buffered media, some of which may contain one or more of the above reagents. Preferably, primers PX1, PX2, P1, P2 and P3 are packaged in a single container. More preferably, at least all of the above components other than buffer are packaged in a single container.

The kit can further include a pair of adapter primers for amplifying the target and reference nucleic acids. One of the primers has a 3'-end portion that is hybridizable to the target and reference nucleic acids and a portion 5' thereof that is not hybridizable with the target or reference nucleic acids and is substantially identical to primer P2. The other of the primers has a 3'-end portion that is hybridizable to the target and reference nucleic acids and a portion 5' thereof that is not hybridizable with the target or reference nucleic acids and is substantially identical to the 3'-end portion Pa of primers P1 and P3. The adapter primers are usually packaged in a container separate from primers P1, P2 and P3.

Alternatively, a kit may also include (a) a primer P2 that is extendable along one of the strands of the target and reference nucleic acid sequences, (b) a primer P4 comprising a 3'-end portion Pa that binds to and is extendable along the other of the strands of the target and reference nucleic acid sequences and a 5'-end portion that does not bind to the target and reference nucleic acid sequences, and (c) a primer P5 which binds to the target and reference nucleic acid sequences at a location downstream, in the 3' direction, of the 3' end portion of primer P4. Preferably, primer P2 can be labeled, but primers P4 and P5 alternatively may be labeled. The kit can also include a reference nucleic acid, which corresponds to a target nucleic acid sequence except for the possible presence of a difference such as a mutation, and reagents for conducting an amplification of target nucleic acid sequence prior to subjecting the target nucleic acid sequence to the methods of the present invention. The kit can also include nucleoside triphosphates and a nucleotide polymerase. The kit can further include particles as described above capable of binding to the label on at least one of the primers. The kit can further include members of a signal producing system and also various buffered media, some of which may contain one or more of the above reagents. Preferably, primers, more preferably, at least all of the above components other than buffer, are packaged in a single container.

The relative amounts of the various reagents in the kits can be varied widely to provide for concentrations of the reagents, which substantially optimize the reactions that need to occur during the present method and to further substantially optimize the sensitivity of the method in detecting a mutation. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some or all of the reagents can be combined in one container where cross-reactivity and shelf life permit. In a particular embodiment of a kit in accordance with the present invention, the reagents are packaged in a single container. The kits may also include a written description of a method in accordance with the present invention as described above.

EXAMPLES

The invention is demonstrated further by the following illustrative examples. Temperatures are in degrees centigrade (°C.) and parts and percentages are by weight, unless otherwise indicated. The following definitions and abbreviations are used herein:

Tris—Tris(hydroxymethyl)aminomethane-HCl (a 10×solution) from BioWhittaker, Walkersville, Md.

Acc-Ab$_{Dig}$—Acceptor beads coupled to the anti-Digoxin antibody for use in an induced luminescence assay Sens-Sav—Sensitizer beads coupled to streptavidin for use in an induced luminescence assay BSA—bovine serum albumin from Gibco BRL, Gaithersburg Md.

bp—base pairs wt (+)—wild type allele mut (−)—mutant allele

+/+—homozygote with 2 normal alleles

−/−—homozygote with 2 mutant alleles

+/−—heterozygote with 1 normal and 1 mutant allele

Target sample—DNA sample to be tested for the presence of a mutation;

Reference sample—DNA sample homozygous for the wt sequence with which target samples are challenged.

sec—seconds hr—hours min—minutes

Buffer A—10 mM Tris-HCl (pH 8.3 at RT), 50 mM KCl, 4 mM MgCl$_2$, 200 µg/ml BSA

Buffer B—10 mM Tris-HCl (pH 8.3 at RT), 50 mM KCl, 20 mM MgCl$_2$, 200 µg/ml BSA Buffer C—0.1M Tris, 0.3M NaCl, 25 mM EDTA, 0.1% BSA, 0.1% dextran T-500, a 1:320 dilution of mouse IgG (HBR-1 from Scantibodies Laboratory Inc., Los Angeles, Calif.), 0.05% Kathon (Rohm and Haas, Philadelphia, Pa.), and 0.01% gentamycin sulfate.

RLU—relative light units nt—nucleotides

MAD—maleimidylaminodextran

Ab—antibody

Sav—streptavidin

MOPS—3-(N-morpholino)propane sulfonic acid hr—hour sulfo-SMCC—sulfosuccinimidyl 4-(N-maleimidomethyl)cyclohexane-1-carboxylate NHS—N-hydroxysuccinimide EDAC—1-ethyl-3-(3-dimethylaminopropyl) carbodiimide hydrochloride DMSO—dimethylsulfoxide MES—morpholinoethanesulfonate rpm—rotations per min EDTA—ethylenediaminetetraacetic acid SATA—N-succinimidyl S-acetylthioacetate BSA—bovine serum albumin from Sigma Chemical Company, St. Louis Mo.

eq—equivalents bp—base pairs $A_{280}$—absorbance at wavelength 280 nanometers

DexAl—dextran aldehyde

DPP—4,7-diphenylphenanthroline

Eu(TTA)$_3$—europium tri-3-(2-thienoyl)-1,1,1-trifluoroacetonate

L or l—liter exo VII—exonuclease VII from *E.coli* (from Amersham Life Science) (USB).

DMF—dimethyl formamide

THF—tetrahydrofuran

MS—mass spectroscopy

NMR—nuclear magnetic resonance spectroscopy

TMSCl—tetramethylsilylchloride

ELISA—enzyme linked immunosorbent assay as described in "Enzyme-Immunoassay," Edward T. Maggio, CRC Press, Inc., Boca Raton, Fla. (1980)

Monoclonal antibodies were produced by standard hybrid cell technology. Briefly, the appropriated immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, dig-BSA conjugate. A number of screening techniques were employed such as, for example, ELISA screens. Selected fusions were then recloned.

Preparation of Beads for Use in an Induced Luminescence Assay

Acc-Ab$_{Dig}$—Acceptor beads coupled to the anti-Digoxin antibody (with 377 antibody molecules per bead) containing either (1) Eu(TTA)$_3$DPP and C-28 Thioxene (Eu Beads)or (2) C-28 Thioxene, 1-Cl-BPEA, and Rubrene (TAR Beads) were used in the following examples. Examples 1–3 were carried out with anti-Dig coupled Eu Beads. The remaining examples were carried out with anti-Dig coupled TAR beads. These beads were prepared as follows:

Preparation of C-28 thioxene:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and was dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS ($C_{42}H_{69}NO_2$): [M-H]$^+$618.6, $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS ($C_{44}H_{71}NOS$): [M-H]$^+$661.6, $^1$H NMR (250 MHz, $CDCl_3$) was consistent with the expected C-28 thioxene product 2-(4-(N,N-di-($Cl_{14}H_{29}$)-anilino)-3-phenyl thioxene.

Preparation of carboxyl acceptor beads containing Eu(TTA)$_3$DPP and C-28 thioxene (Eu beads):

The starting beads were carboxylate modified latex purchased from Seradyn Particle Technology, Indianapolis, Ind. The beads contained Eu(TTA)$_3$DPP prepared as follows: DPP/Eu(TTA)$_3$ was prepared by combining 8.69 g of Eu(TTA)$_3$ . 3H$_2$O (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hour. Toluene was removed under reduced pressure. The ash colored solid was crystallized from 10 ml of toluene to yield 10 grams of DPP/Eu(TTA)$_3$. Absorption spectrum: 270 nm (20,000), 340 nm (60,000) (Toluene) 1.R(KBr): Cm$^{-1}$: 3440(s), 1600(s), 1540(s), 1400 (s), 1300(s). Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM C-28 thioxene and 15.5 mM Eu(TTA)$_3$DPP was added; the beads were stirred for 5 minutes more. At this point 1.0 mL of 0.1N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

Preparation of TAR Beads

The following dye composition was employed: 20% C-28 thioxene (prepared as described above), 1.6%1-chloro-9,10-bis(phenylethynyl)anthracene (1-Cl-BPEA) (from Aldrich Chemical Company) and 2.7% rubrene (from Aldrich Chemical Company). The particles were latex particles (Seradyn Particle Technology, Indianapolis Ind.). The dye composition (240–250 mM C-28 thioxene, 8–16 mM 1-Cl-BPEA, and 20–30 mM rubrene) was incorporated into the latex beads in a manner similar to that described in U.S. Pat. No. 5,340,716 issued Aug. 23, 1994 (the '716 patent), at column 48, lines 24–45, which is incorporated herein by reference. The dyeing process involved the addition of the latex beads (10% solids) into a mixture of ethylene glycol (65.4%), 2-ethoxyethanol (32.2%) and 0.1N NaOH (2.3%). The beads were mixed and heated for 40 minutes at 95° C. with continuos stirring. While the beads are being heated, the three chemiluminescent dyes were dissolved in 2-ethoxyethanol by heating them to 95° C. for 30 minutes with continuous stirring. At the end of both incubations, the dye solution was poured into the bead suspension and the resulting mixture was incubated for an additional 20 minutes with continuous stirring. Following the 20-minute incubation, the beads were removed form the oil bath and are allowed to cool to 40° C.±10° C. The beads were then passed through a 43-micron mesh polyester filter and washed. The dyed particles were washed using a Microgon (Microgon Inc., Laguna Hills, Calif.). The beads were first washed with a solvent mixture composed of ethylene glycol and 2-ethoxyethanol (70%/30%). The beads were washed with 500 ml of solvent mixture per gram of beads. This is followed by a 10% aqueous ethanol (pH 10–11) wash. The wash volume was 400 ml per gram of beads. The beads were then collected and tested for % solid, dye content, particle size, signal and background generation.

Preparation of acceptor beads coated with maleimidylaminodextran (MAD):

Hydroxypropylaminodextran (1NH$_2$/7 glucose) was prepared by dissolving Dextran T-500 (Pharmacia, Uppsala, Sweden) (50 g) in 150 mL of H$_2$O in a 3-neck round-bottom flask equipped with mechanical stirrer and dropping funnel. To the above solution was added 18.8 g of Zn (BF$_4$)$_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran ($1NH_2/7$ glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.mg of Sulfo-SMCC in 1 mL of water. This mixture was incubated for 1 hr at room temperature and used without further purification.

Carboxyl acceptor beads prepared above (99 mg in 4.5 mL water) were added slowly with vortexing to 5.5 mL of MAD aminodextran from above, followed by 1 mL of 200 mg/mL NHS in 50 mM MES, pH 6, 1 mL of 200 mg/mL EDAC in water, and 450 μL of 1 M HCl, final pH 6. The mixture was incubated overnight at room temperature in the dark, then reacted with 200 mg succinic anhydride in 0.5 mL of DMSO for 30 min at room temperature. Freshly opened Surfact-Amps Tween-20 (Pierce Chemical Company, Rockford, Ill.) was added and the beads were centrifuged 30 min at 15,000 rpm in a Sorvall RC-5B centrifuge, washed by centrifugation with three 10 mL portions of 50 mM MOPS, 50 mM EDTA, 0.1% Surfact-Amps Tween-20 (Pierce Chemical Company), pH 7.2, and resuspended in 3 mL of the same.

Coupling MAD coated beads to anti-digoxin monoclonal antibody:

Monoclonal anti-digoxin Ab (prepared as described above) was purified by ABx resin (Baker Chemical Company, Phillipsburg, N.J.) and was dialyzed into 0.15 M NaCl, 5 mM $Na_2HPO_4$, pH 7.4. The anti-digoxin Ab was thiolated by mixing 622 μL (4.28 mg) with 10.2 μL of SATA (1.25 mg/mL in ethanol, 2 eq.), incubating for 1 hr at room temperature and dialyzing cold against 2×2 L of 150 mM NaCl, 10 mM $Na_2HPO_4$, 1 mM EDTA, pH7. The thioacetylated antibody was deacetylated by adding 62.2 μL of hydroxylamine (1 M $H_2NOH$, 50 mM MOPS, 25 mM EDTA, pH 7), bubbling with argon and incubating for 1 hr at room temperature. The product was applied to a Pharmacia PD-10 column (G-25) and eluted with 50 mM MOPS, 50 mM EDTA, pH 7.2, bubbled with argon. After 2.5 mL fore-run, three-1 mL fractions were collected and combined. Recovery of antibody was 3.66 mg or 86% by $A_{280}$. Surfact-Amps Tween-20 (10%) was added to give 0.2% final concentration.

A 1.4 mL aliquot of the thiolated antibody above (1.71 mg antibody) was immediately added to 300 μL (10 mg) of maleimidated beads prepared above plus enough 10% Tween-20 to bring final concentration of the mixture to 0.2%. The tube was purged with argon and incubated overnight at room temperature in the dark. To the above was added 3.4 μL of 1 M $HSCH_2COOH$ in water. After 30 min at room temperature, 6.8 μL of $ICH_2COOH$ (1 M in water) was added. After 30 min 3.5 mL of 0.17M glycine, 0.1M NaCl, 0.1% (v/v) Tween-20, 10 mg/mL BSA, pH 9.2 was added and the beads were centrifuged (30 min at 15,000 rpm), incubated for 3 hr in 5 mL of the same buffer, centrifuged, washed by centrifugation with three-5 mL portions of Buffer C, resuspended in 5 mL of Buffer C and stored under refrigeration. The size of the beads, determined in Buffer C, was 301+/−56 nm. Binding capacity was determined with $^{125}$I-digoxin and was equivalent to 377 antibody molecules per bead.

Preparation of streptavidin coated sensitizer beads (Sens-Sav)

Silicon tetra-t-butyl phthalocyanine was prepared as follows:

Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask an concentrated sulfuric acid (500 mL) was added with stirring. The mixture was stirred for 4 hr. at 60° C. and was then carefully diluted with crushed ice (2000 g). The resulting mixture was filtered and the solid wad washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered.

The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer an a reflux condenser. The mixture was heated under reflux for 1.5 hr. an then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (MS: $[M-H]^+$ 1364.2, absorption spectra: methanol: 674 nm ($\epsilon$180,000): toluene 678 nm, $^1$H NMR (250 MHz, $CDCl_3$): $\delta$: −2.4(m, 12H), −1.3(m, 12H), 0.2–0.9 (m, 54H), 1.8(s, 36H), 8.3(d, 4H) and 9.6 (m, 8H) was consistent with the above expected product.

Sensitizer beads coupled to Streptavidin (2300 Sav/bead)

The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94+/−1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24-40 rubber septum. The beads were stirred at 765 rpm at a temperature of 94+/−1° C. for 40 min.

Silicon tetra-t-butyl phthalocyanine (10.0 g, prepared as above) was dissolved in 300 mL of benzyl alcohol at 60+/−5° C. and 85 mL was added to the above round bottom flask through the septum by means of a syringe heated to 120+/−10° C. at a rate of 3 mL per min. The remaining 85 mL of the phthalocyanine solution was then added as described above. The syringe and flask originally containing the phthalocyanine was rinsed with 40 mL of benzyl alcohol and transferred to round-bottom flask. After 15 min 900 mL of deionized water and 75 mL of 0.1N NaOH was added dropwise over 40 min. The temperature of the oil bath was allowed to drop slowly to 40+/−10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

Sulfo-SMCC (11.55 mg) was dissolved in 0.5 mL distilled water. Slowly, during 10 sec, the above solution was added to 5 mL of stirring aminodextran (Molecular Probes, Eugene, Oreg.) solution (12.5 mg/mL in 50 mM MOPS, pH 7.2). The mixture was incubated for 1 hr at room temperature.

To the stirring solution above was added 5 mL of 20 mg/mL (100 mg) of the sensitizer beads prepared above in distilled water. Then, 1 mL of 200 mg/mL NHS (prepared fresh in 50 mM MES, pH adjusted to 6.0 with 6N NaOH). 200 mg EDAC was dissolved in 1 mL distilled water and this solution was added slowly with stirring to the sensitizer beads. The pH was adjusted to 6.0 by addition of 450 $\mu$L of 1N HCl and the mixture was incubated overnight in the dark. A solution of 100 mg of succinic anhydride in 0.5 mL of DMSO was added to the sensitizer beads and the mixture was incubated for 30 min at room temperature in the dark. To this mixture was added 0.13 mL 10% Tween-20 bringing the final concentration of Tween-20 to 0.1%. The beads were centrifuged for 45 min at 15,000 rpm as above. The supernatant was discarded and the beads were resuspended in 10 mL of buffer (50 mM MOPS, 50 mM EDTA and 0.1% Tween-20, pH 7.2). The mixture was sonicated to disperse the beads. The beads were centrifuged for 30 min as described above, the supernatant was discarded and the beads were resuspended. This procedure was repeated for a total of three times. Then, the beads were resuspended to 40 mg/mL in 2.5 mL of the above buffer, saturated with argon and Tween-20 was added to a concentration of 0.1 %. The beads were stored at 4° C.

Streptavidin was bound to the above beads using 25 mg streptavidin for 100 mg of beads. 25 mg streptavidin (50 mg Aaston solid from Aaston, Wellesley, Mass.) was dissolved in 1 mL of 1 mM EDTA, pH 7.5, and 771 $\mu$L of 2.5 mg/mL SATA in ethanol was added thereto. The mixture was incubated for 30 min at room temperature. A deacetylation solution was prepared containing 1M hydroxylamine-HCl, 50 mM $Na_2PO_4$, 25 mM EDTA, pH 7.0. 0.1 mL of this deacetylation solution was added to the above solution and incubated for 1 hr at room temperature. The resulting thiolated streptavidin was purified on a Pharmacia PD10 column and washed with a column buffer containing 50 mM MOPS, 50 mM EDTA, pH 7.2. The volume of the sample was brought to 2.5 mL by adding 1.5 mL of the above column buffer. The sample was loaded on the column and eluted with 3.5 mL of the column buffer. The thiolated streptavidin was diluted to 5 mL by adding 1.5 mL of 50 mM MOPS, 50 mM EDTA, 0.1% Tween-20, pH 7.2. 5 mL of the thiolated streptavidin solution was added to 5 mL of the sensitizer beads, under argon, and mixed well. The beads were topped with argon for 1 min, the tube was sealed and the reaction mixture was incubated overnight at room temperature in the dark.

To the above beads was added 7.5 mL of 50 mM MOPS, 50 mM EDTA, 0.1% Tween-20, pH 7.2 to bring the beads to 1 mg/mL. The remaining maleimides were capped by adding mercaptoacetic acid at a final concentration of 2 mM. The mixture was incubated in the dark for 30 min at room temperature. The remaining thiols were capped by adding iodoacetic acid at a final concentration of 10 mM and the mixture was incubated at room temperature for 30 min in the dark. The beads were centrifuged for 30 min at 15,000 rpm as above for a total of three times.

Example 1

In this example a 3-bp deletion, $\Delta$F508, in exon 10 (the most frequently occurring mutation) of the human cystic fibrosis gene (CFTR) was studied.

Human genomic DNA samples (50 ng) (from Roche Molecular Systems, Alameda Calif., except for $\Delta$F508/$\Delta$F508 homozygote(−/−), which was from Coriell Institute for Medical Research, Camden N.J.) were amplified by PCR with the following primers:

Primer PX2: 5'-CAAGTGMTCCTGAGCGTGA-3' (SEQ ID NO. 1) and

Primer PX1: 5'-CTAACCGATTGMTATGGAGCC-3' (SEQ ID NO. 2).

Both primers were from Oligos Etc., Inc., Wilsonville, Oreg. The amplification was carried out in a 96-well block of a UNO thermocycler from Biometra, Tampa Fla. to generate a PCR product 340-bp in length. After the initial denaturation step (95° C. for 4 min), 35 cycles were performed consisting of 94° C. for 30 sec, 64° C. for 1 min and 72° C. for 1 min.

The resulting amplicons were diluted 1:1000, and 1 $\mu$l (per 50 $\mu$l reaction volume) aliquots of these dilutions were amplified in a second round of PCR (20 cycles under the same conditions as in step 1) using a mixture of primers P2B (or P2D), P1 and P3. The resulting PCR products are 220-bp in length.

P2: 5'-CTCAGTTTTCCTGGATTATGCC-3' (SEQ ID NO. 3)

P2D: digoxygenin-labeled P2 from Genosys Biotechnologies, Inc., Woodlands, Tex.

P2B: biotinylated P2 from Oligos Etc., Inc., Wilsonville, Oreg.

P1: 5'-ACCATGCTCGAGATTACGAGCTMCCGATTGAAT ATGGAGCC-3' (SEQ ID NO. 4) from Oligos Etc., Inc., Wilsonville, Oreg.

P3: 5'-GATCCTAGGCCTCACGTATTCTAACCGATTGAAT ATGGAGCC-3', (SEQ ID NO. 5) from Oligos Etc., Inc., Wilsonville, Oreg.

The underlined sequences represent tail B1 (for primer P1) and tail A1 (for primer P3). Pa as part of primers P1 and P3 is identical to PX1.

WT1 below was used as the reference sample and amplified with primers P2D, P1 and P3.

All the test samples were amplified with primers P2B, P1 and P3.

In the next step (banch migration) equal volumes of test and reference amplicons were mixed and the mixture was over-layed with mineral oil. The reaction mixture was heated for 1 min at 95° C. (denaturation) followed by 30 min at 65° C.

Detection, was carried out as follows: Acc-Ab$_{Dig}$ and Sens-Sav beads were titrated with varying amounts of the branch migration reaction mixtures with varying ratios of test sample to reference sample to assure a linear response. Amounts of the components were as follows.

A 2 $\mu$l aliquot of the branch migration reaction mixture was combined with 100 $\mu$l buffer B containing 5 $\mu$l (10 $\mu$g) Sens-Sav and 5 $\mu$l (10 $\mu$g) Acc-Ab$_{Dig}$ beads and incubated for 5 min at 37° C. The reaction mixture was then irradiated with a 150 watt Xenon lamp for 3 sec (3 cycles of 1 sec illumination and 1 sec waiting time) and the signal was then read.

TABLE 1

| Sample | Signal (RLU) |
| --- | --- |
| Blank | 4790 |
| WT1 (+/+) | 19834 |
| WT2 (+/+) | 18530 |
| WT3 (+/+) | 19496 |
| WT4 (+/+) | 19972 |
| WT5 (+/+) | 18460 |
| WT6 (+/+) | 19380 |
| WT7 (+/+) | 17980 |
| ΔF508/ΔF508 homozygote (−/−) | 1341990 |
| WT/ΔF508 heterozygote 1 (+/−) | 524236 |
| WT/ΔF508 heterozygote 2 (+/−) | 625440 |

Example 2

Detection of mutations in exon 10 of the cystic fibrosis gene.

In this example the labeled and tailed amplification products for branch migration were prepared directly from genomic DNA.

Human genomic DNA samples (50 ng) (from Roche Molecular Systems, Alameda Calif., except for ΔF508/ΔF508 homozygote(−/−), which was from Coriell Institute for Medical Research, Camden N.J.) were amplified with the following primers:

P2: 5'-CTCAGTTTTCCTGGATTATGCC-3' (SEQ ID NO. 3)

P2D: digoxygenin-labeled P2 from Genosys Biotechnologies, Inc., Woodlands, Tex.

P2B: biotinylated P2 from Oligos Etc., Inc., Wilsonville, Oreg.

P1: 5'-ACCATGCTCGAGATTACGAGCTMCCGATTGMT ATGGAGCC-3' (SEQ ID NO. 4) from Oligos Etc., Inc., Wilsonville, Oreg.

P3: 5'-GATCCTAGGCCTCACGTATTCTAACCGATTGMT ATGGAGCC- 3', (SEQ ID NO. 5) from Oligos Etc., Inc., Wilsonville, Oreg.

The underlined sequences are the 5'-end portions of primers P1 and P3 which are not complementary to the target and reference sequences or to each other.

Test samples were amplified with the primers P2B (or P2D), P1 and P3. The resulting PCR products are 220-bp in length.

PCR amplification was carried out as follows: The amplification was carried out in a 96-well block of a UNO thermocycler from Biometra, Tampa Fla. The reaction volume was 50 $\mu$l. After the initial denaturation step (95° C. for 4 min), 35 cycles were performed consisting of 94° C. for 30 sec, 64° C. for 1 min and 72° C. for 1 min.

Branch migration was carried out as follows: 2 $\mu$l of each of the reaction mixtures (after PCR amplification) was combined and 8 $\mu$l of buffer A containing 28 mM MgCl$_2$ was added (final concentration 20 mM MgCl$_2$). The reaction mixture was overlaid with 5 $\mu$l mineral oil incubated at 94 for 2 min. to denature DNA and further incubated 30 min at 65° C. for formation of partial duplexes and strand exchange.

The following protocol was utilized for detection of the quadramolecular complex C: Acc-Ab$_{Dig}$ and Sens-Sav beads were titrated with varying amounts of the branch migration reaction mixtures with varying ratios of test sample to reference sample to assure a linear response. Optimal amounts of the components were as follows:

A 2 $\mu$l aliquot of the branch migration reaction mixture was combined with 100 $\mu$l Buffer B containing 5 $\mu$l (10 $\mu$g) Sens-Sav and 5 $\mu$l (10 $\mu$g) Acc-Ab$_{Dig}$ beads and incubated for 5 min at 37° C. The reaction mixture was then irradiated with a 150 watt Xenon lamp for 3 sec (3 cycles of 1 sec illumination and 1 sec waiting time) and the signal was then read.

The results are summarized in the Table 2.

TABLE 2

| Sample | Signal (RLU) |
| --- | --- |
| Blank | 7696 |
| WT1 (+/+) | 34980 |
| WT2 (+/+) | 34790 |
| WT3 (+/+) | 35166 |
| WT4 (+/+) | 32692 |
| WT5 (+/+) | 33846 |
| WT6 (+/+) | 38470 |
| WT7 (+/+) | 36374 |
| ΔF508/ΔF508 homozygote (−/−) | 1824820 |
| WT/ΔF508 heterozygote 1 (+/−) | 447710 |
| WT/ΔF508 heterozygote 2 (+/−) | 812436 |

Example 3

In this example the simplified direct protocol described in Example 2 for the detection of the ΔF508 3-bp deletion was applied to the detection of 4 point mutations in exon 11. Genomic DNA having the following point mutations within exon 11 of the CFTR gene used herein:

Heterozygous DNA with one wild type (wt) allele and one of the following mutant alleles:

G542X (G>T substitution) from Roche Molecular Systems, Alameda, Calif.;

G551D (G>A substitution) from Roche Molecular Systems, Alameda, Calif.;

R553X (C>T substitution) from Roche Molecular Systems, Alameda, Calif.;

R560T (G>C substitution) from Roche Molecular Systems, Alameda, Calif.

Homozygous DNA:

G542X/G542X from Coriell Institute for Medical Research, Camden, N.J.

Two different pairs of labeled and tailed primers were used to prepare amplification products for branch migration directly from genomic DNA:

Primer set I:

Primer P2: 5'-TAGMGGMGATGTGCCTTTCA-3' (SEQ ID NO. 6)

P2D and P2B: digoxygenin and biotin-labeled P2, respectively.

Primer P1: 5'-ACCATGCTCGAGATTACGAGTTCTTMCCCACTAGCCATAAA-3' (SEQ ID NO. 7)

Primer P3: 5'-GATCCTAGGCCTCACGTATTTTCTTMCCCACTAGCCATAAA-3' (SEQ ID NO. 8)

The underlined sequence represent the 5'-end portion of primers P1 and P3 which are not complementary to the target or reference sequence or to each other.

Primer set II:

Primer P2: 5'-TTACATTAGAAGGAAGATGTGCCT-3' (SEQ ID NO. 9)

P2D and P2B: digoxygenin and biotin-labeled P2, respectively.

Primer P1: 5'-ACCATGCTCGAGATTACGAGGTGATTCTTMCCCACTAGCCA-3' (SEQ ID NO. 10)

Primer P3: 5'-GATCCTAGGCCTCACGTATTGTGATTCTTMCCCACTAGCCA-3' (SEQ ID NO. 11)

The underlined sequence represent the 5'-end portion of the primers P1 and P3 which is not complementary to the target or reference sequence or to each other.

All primers were from Oligos Etc., Inc., Wilsonville, Oreg.

PCR from genomic DNA, branch migration and detection were carried out exactly as described in Example 2 (37 PCR cycles were performed). The resulting PCR products were 333 bp and 343 bp in length, respectively.

WT1 below was used as the reference sample and amplified with primers P2D, P1 and P3 of primer set I or primer set II, respectively (primer set I and primer set II, respectively, in Table 3 below).

All the test samples were amplified with primers P2B, P1 and P3 of primer set I and primer set II, respectively (Set I and Set II, respectively, in Table 3 below).

TABLE 3

| Sample | Signal (RLU) | |
| --- | --- | --- |
| | Set I | Set II |
| Blank | 7384 | 8396 |
| WT1 (+/+) | 45456 | 56210 |
| WT2 (+/+) | 52480 | 49174 |
| WT3 (+/+) | 65172 | 56992 |
| WT4 (+/+) | 30778 | 88682 |
| WT5 (+/+) | 71906 | 63398 |
| G542X/G542X (−/−) | 1797530 | 1148180 |
| G542X/WT (+/−) | 695056 | 473342 |
| G551D/WT (+/−) | 902458 | 499874 |
| G553X/WT (+/−) | 859416 | 571882 |
| G560T/WT (+/−) | 1030630 | 587710 |

In another experiment, the test and the reference genomic DNA samples were co-amplified with a mixture of primers P2B, P2D, P1 and P3 of primer set I. The results are summarized in Table 4 below.

TABLE 4

| Sample | Signal (RLU) |
| --- | --- |
| Blank | 7384 |
| WT1 (+/+) | 18166 |
| WT2 (+/+) | 16462 |
| WT3 (+/+) | 20282 |
| WT4 (+/+) | 19106 |
| WT5 (+/+) | 21790 |
| G542X/G542X (−/−) | 640182 |
| G542X/WT (+/−) | 265984 |
| G551D/WT (+/−) | 294094 |
| G553X/WT (+/−) | 302366 |
| G560T/WT (+/−) | 336964 |

Example 4

To make non-specific PCR products undetectable, an alternative primer scheme was employed for the detection of a mutation in exon 10 of the human cystic fibrosis gene. Here, the alternative primer scheme utilizes two reverse primers P4 and P5 wherein P4 has a 3' end portion which binds to one strand of the target or reference sequence at a location upstream of primer P5. In this example, the alternative primer scheme is compared with the primer scheme of Example 2.

The primers P2B, P2D, P1 and P3 for the original primer scheme are the same as in Example 2. Primers for the alternative scheme are P2B, P2D, P4 and P5. For an unbiased comparison between alternative and the original schemes the forward primers in both schemes are the same and P5 is identical to the 3' portion Pa of primers P1 and P3.

P2B and P2D—forward primers for exon 10, biotinylated and digoxigenin-labeled at their 5'-ends, respectively, where P2 is the following sequence:

5'-CTCAGTTTTCCTGGATTATGCC -3' (SEQ ID NO. 3)

The reverse primers (P1), (P3), (P4) and (P5), had the following sequences:

P1: 5'-ACCATGCTCGAGATTACGAGCTAACCGATTGAATATGGAGCC -3' (SEQ ID NO. 4) where the tail sequence is underlined P3: 5'-GATCCTAGGCCTCACGTATTCTMCCGATTGMTATGGAGCC -3' (SEQ ID NO. 5) where the tail sequence is underlined.

The tails are B1 and A1, respectively, as in FIG. 3.

P4: 5'-AGCCTAATCGTCCACGATGTATAAATATATMTTTGGGTAGTGT-3' (SEQ ID NO. 12) here the tail sequence is underlined

P5: 5'-CTAACCGATTGAATATGGAGCC -3' (SEQ ID NO. 13)

PCR amplification was carried out using a TRIO thermocycler from Biometra (Tampa, Fla.). Thirty-five amplification cycles were performed, each consisting of 30 sec. at 94° C., 1 min. at 54° C. and 1 min. at 72° C. The reaction volume of 20 µl contained 0.5 U thermostable Pfu polymerase from Stratagene (San Diego, Calif.). The total reaction volume for PCR with wax-mediated hot start was 40 µl. The buffer contained 10 mM Tris-HCl, pH 8.3, 50 mM KCl, 4 mM MgCl$_2$ and 200 µg/ml BSA (buffer A).

Primers (125 nM each) were used in PCR amplification to generate an amplicon 220 bp in length. Wild type (wt) homozygote and a compound heterozygote ΔF508/R553X (mut) genomic DNA samples were from Coriell Institute for Medical Research (Camden, N.J.). 1 ng/µl genomic DNA were present in each PCR reaction.

After PCR, the samples were heat denatured and allowed to reanneal and undergo strand exchange by branch migration (2 min. at 94° C. followed by 30 min. at 65° C.). This last program was linked to the PCR program so that branch migration immediately followed amplification with no need to open the tubes.

2 μl aliquots were mixed with 50 μl of the induced luminescent assay bead suspension (25 μg S-Sav and 12.5 μg CL-Mab$_{Dig}$ per 1 ml buffer). After 30 min. incubation at 37° C., the induced luminescent assay signals were read using an instrument capable of processing 8-tube PCR strips.

Table 5 illustrates the advantage of this alternative primer scheme over the scheme of Example 2. The wild type and mutant samples were run in duplicates.

TABLE 5

| | LOCI Signal (RLU) | | | |
|---|---|---|---|---|
| | w/o Hot Start | | with Hot Start | |
| | Column | | | |
| | 1 Original | 2 Alternative | 3 Original | 4 Alternative |
| wt | 556122 | 9236 | 64464 | 7744 |
| wt | 511318 | 11446 | 35096 | 9200 |
| mut | 893474 | 209052 | 430266 | 266062 |
| mut | 912204 | 233812 | 424330 | 272332 |

Column 1 confirms our previous knowledge that implementation of a hot start procedure is preferred for the branch migration inhibition assay according to the primer design of Example 2. There is essentially no discrimination between the wt and the mutant samples due to a very high background. The use of wax beads as a means of accomplishing hot start results in a considerable drop in background (wt) signal for this primer scheme (column 3). However, the background is still 2–4 times higher than usual. This is due to the fact that PCR was performed at a very low stringency: the cycle annealing temperature of 54° C., which is 10° C. lower than the optimal for this primer set temperature of 64° C. This low cycle annealing temperature was chosen because the sequence-specific region of primer P4 happens to have a low T$_m$ due to its high AT content.

A major improvement is observed when the reverse primers are aligned according to the alternative primer scheme. Even without a hot start, the background is as low as it can be (the signal generated by the beads with no sample added) The data in column 2 illustrate this improvement. Implementation of a hot start does not afford further improvement for this alternative primer scheme (column 4).

Example 5
Alternative primer scheme for several cystic fibrosis gene exon 11 amplicons.

PCR conditions were the same as described above for Example 4. PCR reactions were run without a hot start. The same genomic DNA samples as in Example 4 were used. Two sets of forward (P2) primers and two sets of reverse (P4 and P5) primers were used for detection of exon 11 mutations using the alternative scheme designed to reduce signal due to non specific amplification. Use of different combinations of forward primer and either the first set or the second set of P4 and P5 primers allow production of amplification products of various lengths. All primers were from Oligos Etc., Inc., Wilsonville, Oreg.

The first set of forward primers included: P2B-1 and P2D-1 —forward primers for exon 11 (columns 1 and 3 in Table 6), biotinylated and digoxigenin-labeled at their 5'-ends, respectively, where P2-1 is the following sequence:
5'-GCCTTTCAAATTCAGATTGAGC-3' (SEQ ID NO. 14)

The first set of reverse primers (FIG. 7), P4-1 and P5-1, had the following sequences:
P5-1: 5'-GACATTTACAGCAAATGCTTGC-3' (SEQ ID NO. 15)
P4-1: 5'-AGACGACGTCTAGTCATTGCAATAGACCAATAATTAGTTATTCA-3' (SEQ ID NO. 16) where the tail sequence is underlined P2B-2 and P2D-2—the second set of forward primers for exon 11 (columns 2 and 4 in Table 6), biotinylated and digoxigenin-labeled at their 5'-ends, respectively, where P2-2 is the following sequence:
5'-CAACTGTGGTTAAAGCAATAGTGT-3' (SEQ ID NO. 17)

The second set of reverse primers P4-2 and P5-2 had the following sequences:
P5-2: 5'-GCACAGATTCTGAGTAACCATAAT -3' (SEQ ID NO. 18)
P4-2: 5'-ATGACTTGCTAAGTGCTATGACTCCTCTACCAAATCTGGATACTATAC-3' (SEQ ID NO. 19) where the tail sequence is underlined In this example, two separate PCR reactions were run for each reverse primer (5 μl of is each reaction were mixed together and subjected to BMI conditions: 2 min. at 94° C. followed by 30 min. at 64° C.). The data presented in Table 6 is as follows: data in column 1 was obtained by PCR amplification using the following primer combinations: P2B-1, P2D-1, P4-1 and P5-1. Data in column 2 was obtained by PCR amplifications using the following primer combinations: P2B-2, P2D-2, P4-1 and P5-1. Data in column 3 was obtained by PCR amplification using primer combinations: P2B-1, P2D-1, P4-2 and P5-2. Data in column 4 was obtained by PCR amplification using primer combinations: P2B-2, P2D-2, P4-2 and P5-2

The results are summarized in Table 6. Acceptably low backgrounds demonstrate that this alternative primer scheme is applicable to four different exon 11 amplicons and is superior to the original primer scheme using primers P2, P1 and P3 of Example 3, in that it performs well at low PCR stringency (cycle annealing temperature 54° C. as opposed to 64° C. normally used for respective primers in Example 3) and, at least for these particular amplicons, does not require a hot start.

TABLE 6

| | LOCI Signal (RLU) | | | |
|---|---|---|---|---|
| | 1 | 2 | 3 | 4 |
| amplicon length (bp) | 203 | 296 | 372 | 425 |
| wt | 6582 | 8790 | 10356 | 11200 |
| wt | 6642 | 8216 | 11568 | 11164 |
| mut | 861976 | 116558 | 317990 | 137276 |
| mut | 924380 | 205214 | 268450 | 85810 |

Example 6
Optimization of the ratio of the two reverse primers in alternative primer scheme.

This example presents the result of a study designed for the optimization of the ratio of these primers for optimal detection of mutations in cystic fibrosis gene, exon 11. The DNA samples for this example is the same as that for the previous example, and the primers used are primers P2B-1, P2D-1, P4-1 and P5-1 of that example.

Primers P4 and P5 used in the alternative primer scheme (FIG. 7) compete with each other in PCR as described above. Hence, their balanced performance in a mixture is desired and may depend on their relative thermodynamic parameters. Ideally, to maximize the yield of signal-generating four-stranded structures, the amounts of the amplicons generated by the forward primer, P2, and each of the two reverse primers, P4 and P5, should be equal. Therefore, the absolute value of the signal in an induced luminescence assay is a good criterion for optimizing the ratio. For example, the absence of a signal for mutants (provided that amplification did not fail, as judged by gel electrophoresis) means that one of the reverse primers took over completely. In a typical optimization experiment, several different ratios of concentrations of primer P5 to primer P4 are examined at various PCR cycle annealing temperatures ($T_a$).

An example of such experiment is shown below (Table 7) for the detection of mutations in exon 11. Primer P2B-1 and primer P2D-1 were each present at 125 nM. The total concentration of the two reverse primers (P4-1+P5-1) was 250 nM.

TABLE 7

| Ratio of P5/P4 | 0.1 | 0.33 | 1 | 3 | 9 | 15 | 19 |
|---|---|---|---|---|---|---|---|
| $T_a$ 52° C. | | | | | | | |
| wt | 13992 | 6590 | 8544 | 8614 | 14986 | 17548 | 14208 |
| wt | 8802 | 6746 | 7910 | 6772 | 15754 | 17544 | 11422 |
| mut | 7448 | 10322 | 8132 | 32234 | 327774 | 406186 | 348478 |
| mut | 7188 | 8656 | 8662 | 29520 | 299760 | 376970 | 328760 |
| $T_a$ 55° C. | | | | | | | |
| wt | 5780 | 8300 | 8708 | 9782 | 11164 | 12538 | 14460 |
| wt | 8022 | 8944 | 11506 | 9694 | 13812 | 13750 | 11946 |
| mut | 11782 | 11378 | 12354 | 147874 | 396414 | 503806 | 142618 |
| mut | 8736 | 12042 | 16238 | 128816 | 426710 | | 105494 |
| $T_a$ 58° C. | | | | | | | |
| wt | 8768 | 7250 | 8610 | 9704 | 10076 | 10898 | 11788 |
| wt | 5910 | 4816 | 7538 | 9234 | 10956 | 10640 | 13004 |
| mut | 7504 | 8944 | 11880 | 199796 | 344222 | 268254 | 113748 |
| mut | 10784 | 10388 | 11118 | 211828 | 332226 | 270942 | 95674 |

Table 7 shows that the short outer primer, P5, must be present at higher concentrations (3- to 20-fold) than the inner, long primer, P4, in spite of a higher $T_m$ and 3'-terminal stability of the former (these parameters differ by 13° C. and −1.6 kcal/mol, respectively). At higher $T_a$ the optimum is achieved at lower ratio. Similar experiments with other amplicons show that a balanced performance of the two reverse primers can usually be achieved by varying their relative concentrations.

Example 7

Performance of the alternative BMI scheme for detection of mutation in exon 10 of CFTR gene, using non-contiguous reverse primers.

To demonstrate the tailed/untailed primer pairs need not be contiguous in order for the alternative scheme to function, three tailed reverse primers, P4, were designed: (1) P4-1—which primes a site contiguous to that site bound by the untailed primer P5; (2) P4-2—which primes a site which is separated from that site bound by the same untailed primer (a 15 base separation from the P5 priming site); (3) P4-3—which primes a site overlapping that site bound by the untailed primer (a 7 base overlap with P5 priming site).

In this particular example, the labeled forward primers P2B and P2D were used with each reverse primer, tailed or untailed, to separately amplify the desired sequence, a portion of exon 10 of the CFTR gene. The product amplicons were mixed for subsequent BMI analysis as will be described in the following. All primers were prepared by Oligos Etc. Inc., Wilsonville, Oreg.

P2B and P2D—forward primers for exon 10, biotinylated and digoxigenin-labeled at their 5'-ends, respectively, have the following sequence:
5'-CTCAGTTTTCCTGGATTATGCC-3' (SEQUENCE I.D. NO. 3)

The tailed reverse primers (P4-1), (P4-2), and (P4-3), have the following sequences:
P4-1—5'-AGCCTAATCGTCCACGATGTATAAATATATAATT TGGGTAGTGT-3' (SEQ ID NO. 20) where the tail is underlined.
P4-2—5'-AGCCTAATCGTCCACGATGTATGTAGTGTGAA GGGTTCATA-3' (SEQ ID NO. 21) where the tail is underlined.
P4-3—5'-AGCCTAATCGTCCACGATGTATTGGAGCCAAAT ATATAATT-3' (SEQ ID NO. 22) where the tail is underlined.

The non-tailed reverse primer, P5, have the following sequence:
P5—5'-CTAACCGATTGAATATGGAGCC-3' (SEQ ID NO. 23).

PCR amplification was carried out using a TRIO thermocycler from Biometra (Tampa, Fla.). Thirty-five amplification cycles were performed, each consisting of 30 sec. at 94° C., 1 min. at 54° C., and 1 min. at 72° C. The reaction volume of 20 μl contained 0.2 U thermostable Pfu polymerase from Stratagene (San Diego, Calif.). No hot start method was employed. The buffer contained 10 mM Tris-HCl, pH 8.3, 50 mM KCl, 4 mM MgCl$_2$, and 200 μg/ml BSA (buffer A).

The labeled P2B/P2D pair was used in PCR amplification with P4-1, P4-2, P4-3, or P5 (all primers used at 125 nM each), to generate amplicons of 200, 184, 207, and 200 bp, respectively. Wild type (wt) homozygote and a compound heterozygote ΔF508/R553X (mut) genomic DNA samples were purchased from Coriell Institute for Medical Research (Camden, N.J.). 20 ng genomic DNA were present in each PCR reaction.

After PCR, 5 μl aliquots of each P5-containing reaction were mixed with 5 μl of the corresponding P4-1-containing reaction mixture. Likewise, 5 μl aliquots of each P5-containing reaction were mixed with 5 μl of the corresponding (P4-2)-containing reaction mixture, and 5 μl aliquots of each P5-containing reaction were mixed with 5 μl of the corresponding P4-3-containing reaction mixture. Each new sample mix was heat denatured, allowed to reanneal, and undergo strand exchange by branch migration (2 min. at 95° C. followed by 30 min. at 65° C.).

2 μl aliquots of each reaction mixture were mixed with 50 μl of the induced luminescent assay bead suspension (2.325 μg Sens-Sav and 1.125 μg Acc-Ab$_{Dig}$ each). After 30 min. incubation at 37° C., the induced luminescent assay signals were read using an instrument capable of processing 8-tube PCR strips.

Table 8 illustrates the effectiveness of using the alternative primer scheme with separate amplification of contiguous or non-contiguous primers. The wild type and mutant samples were run in triplicate:

TABLE 8

| Reverse Primer Pair | DNA Sample | LOCI Signal (RLU) | Ratio of Mutant Signal o WT Signal |
|---|---|---|---|
| P5/P4-1 (contiguous) | wt | 5806 | 38.6-fold |
| | wt | 7376 | |
| | wt | 7548 | |
| | mut | 284922 | |
| | mut | 273018 | |
| | mut | 241740 | |
| P5/P4-2 (gapped) | wt | 16402 | 27.0-fold |
| | wt | 12000 | |
| | wt | 15252 | |
| | mut | 354264 | |
| | mut | 403728 | |
| | mut | 421218 | |
| P5/P4-3 (overlapping) | wt | 8256 | 21.6-fold |
| | wt | 9252 | |
| | wt | 8976 | |
| | mut | 200456 | |
| | mut | 189290 | |
| | mut | 182364 | |

The above signals clearly demonstrate that separate amplification of non-contiguous primer pairs may be used in the alternative primer scheme. As can be seen, all three sets of primer pairs resulted in good discrimination between the signals observed with mutant samples and those observed with wild type samples, with ratios of 38.6, 27.0, and 21.6, for contiguous primers, gapped primers, and overlapping primers, respectively.

Example 8

Optimization of the performance of the alternative BMI scheme for detection of mutation in exon 10 of CFTR gene, using non contiguous reverse primers.

The objective of the present example is to demonstrate that non-contiguous primer pairs, CFTR P4 and P5, can function when combined in the same reaction tube. Primers P5/P4-1 (contiguous pair), P5/P4-2 (gapped pair), and P5/P4-3 (overlapping pair), were each used in combination with the labeled forward primer pair, P2B/P2D, to amplify the desired sequence, a portion of exon 10 of the CFTR gene. In order to optimize co-amplification using the two reverse primers, various concentration ratios of the reverse primer pairs were employed.

The sequences of the labeled forward primers, P2B and P2D, and P4, the tailed reverse primers, P4-1, P4-2, P4-3, and P5, the untailed reverse primer, are listed and discussed in Example 7.

PCR amplification was carried out using a T3 thermocycler from Biometra (Tampa, Fla.). Thirty-eight amplification cycles were performed, each consisting of 30 sec. at 94° C., 1 min. at 54° C., and 1 min. at 72° C. The reaction volume of 18 μl contained 0.36 U thermostable Pfu polymerase from Stratagene (San Diego, Calif.). The total reaction volume for PCR with wax-mediated hot start was 36 μl. The buffer contained 10 mM Tris-HCl, pH 8.3, 50 mM KCl, 4 mM MgCl$_2$, and 200 μg/ml BSA (buffer A).

The labeled P2B/P2D primers (125 nM of each forward primer) were used in PCR amplification with the varying ratios of the P5/P4-1 pair, the P5/P4-2 pair, and the P5/P4-3 pair (all reverse primer pairs used at a total of 250 nM), to generate two amplicons each of 200 bp/200 bp, 184 bp/200 bp, and 207 bp/200 bp, respectively. Ratios of the untailed (P5) primer to the corresponding tailed primer (P4-1, P4-2, or P4-3) used in the amplification reactions were 1:3, 1:1, 3:1, and 9:1. Wild type (wt) homozygote and a compound heterozygote ΔF508/R553X (mut) genomic DNA samples were purchased from Coriell Institute for Medical Research (Camden, N.J.). 36 ng of each of the genomic DNA samples were present in each of the respective PCR reaction.

After PCR, samples were heat denatured, then allowed to reanneal and undergo strand exchange by branch migration (2 min. at 95° C., followed by 30 min. at 65° C.). This last program was linked to the PCR program permitting branch migration to immediately follow amplification with no need to open the tubes.

2 μl aliquots of each reaction mixture was mixed with 50 μl of the induced luminescent assay bead suspension (2.325 μg Sens-Sav and 1.125 μg Acc-Ab$_{Dig}$ each). After 30 min. incubation at 37° C., the induced luminescent assay signals were read using an instrument capable of processing 8-tube PCR strips.

Table 9 illustrates the optimization and effectiveness of using the alternative primer scheme with simultaneous amplification of contiguous or non-contiguous primer pairs in the same tube. The wild type and mutant samples were run in duplicate.

TABLE 9

| Reverse Primer Pair | DNA Sample | LOCI Signal (Ratio of P5 to Tailed Primer P4) | | | |
|---|---|---|---|---|---|
| | | 1:3 | 1:1 | 3:1 | 9:1 |
| P5/P4-1 (contiguous) | wt | 8928 | 33056 | 71506 | 69580 |
| | wt | 8054 | 39996 | 67294 | 60814 |
| | mut | 15946 | 703178 | 342828 | 92338 |
| | mut | 29068 | 330934 | 357652 | 84402 |
| P5/P4-2 (gapped) | wt | 59276 | 38144 | 82268 | 58378 |
| | wt | 53396 | 39992 | | 61370 |
| | mut | 63600 | 41652 | 866904 | 379528 |
| | mut | 72516 | 41208 | 817106 | 383382 |
| P5/P4-3 (overlapping) | wt | 11830 | 59822 | 68154 | 71088 |
| | wt | 13230 | 56868 | 69926 | 73036 |
| | mut | 16710 | 850350 | 449364 | 134216 |
| | mut | 14482 | 829352 | 373474 | 130722 |

The above signals demonstrate that simultaneous amplification of contiguous and non-contiguous primer pairs in the same tube may be used in the alternative primer scheme. As can be seen, the ratios of all three reverse primer pairs were optimized, resulting in acceptable discrimination between the signals observed with mutant samples and those observed with wild type samples for at least one condition, each. That is, with the contiguous primer pair, P5/P4-1, good discrimination was observed with a P5 to P4-1 ratio of 1:1, while acceptable discrimination was observed when employing a 3:1 ratio of P5 to P4-2 for the gapped pair, or 1:1 ratio of P5 to P4-3 for the overlapping pair. These results demonstrate the feasibility of using gapped or overlapping pairs of primers designed for this alternative scheme.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the claims.

What is claimed is:

1. A method for detecting the presence of a difference between a target nucleic acid sequence and a reference nucleic acid sequence comprising:

(a) amplification of the target sequence by polymerase chain reaction, using a primer P2, a primer P4 having a 3' portion which hybridizes to the target sequence and a 5' tail portion T which is not complementary to the target, and a primer P5 which hybridizes to the target at a location in the 3' direction from a sequence which hybridizes to said 3' portion of primer P4; wherein either:

primer P2 is a mixture of primer P2 with a first label and primer P2 with a second label, or primer P4 has a first label and primer P5 has a second label;

(b) forming a tailed target partial duplex of the target sequence, said duplex having one of said first label or said second label, and a tail of two non-complementary regions wherein a first region is the sequence P5 or its complement and the second region is the sequence T or its complement;

(c) amplification of the reference sequence by polymerase chain reaction, using a primer P2, a primer P4 having a 3' portion which hybridizes to the reference sequence and a 5' tail portion T which is not complementary to the reference, and a primer P5 which hybridizes to the reference substantially adjacent, in the 3' direction, to a sequence which hybridizes to said 3' portion of primer P4, wherein either:

primer P2 is a mixture of primer P2 having a first label and primer P2 having a second label, or primer P4 has a first label and primer P5 has a second label;

(d) forming a tailed target partial duplex of the reference sequence, said partial duplex having one of said first label or said second label, and a tail of two non-complementary strands wherein a first strand is the sequence P5 or its complement and the second strand is the sequence T or its complement;

(e) forming a complex comprising said tailed target sequence and said tailed reference sequence in double stranded form, wherein said complex comprises at least one pair of said non-complementary strands and each of said tailed target sequence and said tailed reference sequence has one of said labels, (f) detecting the association of said labels as part of said complex, wherein detection of the association detects the presence of the difference.

2. The method of claim 1 wherein said labels are selected from the group consisting of oligonucleotides, enzymes, dyes, fluorescent molecules, chemiluminescers, coenzymes, enzyme substrates, radioactive groups, small organic molecules and solid surfaces.

3. The method according to claim 1 wherein said sequence on the target or reference which hybridizes to said 3' portion of primer P4 is immediately adjacent to a sequence of the target or reference which hybridizes to primer P5.

4. The method according to claim 1 wherein said sequence on the target or reference which hybridizes to said 3' portion of primer P4 partially overlaps a sequence of the target or reference which hybridizes to primer P5.

5. The method according to claim 1 wherein said sequence on the target or reference which hybridizes to said 3' portion of primer P4 is not adjacent to a sequence of the target or reference which hybridizes to primer P5.

6. The method according to claim 1 wherein said amplification step (c) is carried out in the same reaction medium as that used for step (a).

7. The method according to claim 1 wherein the first label is the same as the second label.

8. A method of preparing a DNA partial duplex having a portion at an end thereof that has two predefined non-complementary single stranded sequences, the method comprising:

combining in a first combination a nucleic acid sequence, a polymerase, nucleoside triphosphates and primers P2 and P5, wherein said primer P2 hybridizes to and is extendable along a first strand of the nucleic acid sequence, and said primer P5 hybridizes to and is extendable along a second strand of the nucleic acid sequence, combining in a second combination said nucleic acid sequence, said polymerase, and said nucleoside triphosphates, said primer P2 and primer P4 having a 3' portion which hybridizes to said second strand, and a 5' tail portion T which is not complementary to said first strand or said second strand, said 3' portion of primer P4 hybridizing to said second strand at a location in the 5' direction from a sequence which hybridizes to said primer P5;

subjecting said first and second combinations to temperature cycling to extend said primers, combining said first combination with said second combination to form a DNA partial duplex having non-complementary single stranded sequences of T or its complement and P5 or its complement.

9. The method of claim 8 wherein said first combination and said second combination are combined prior to subjecting said combinations to temperature cycling.

10. The method according to claim 8 wherein said sequence which hybridizes to primer P5 is immediately adjacent a sequence which hybridizes to said 3' portion of primer P4.

11. The method according to claim 8 wherein said sequence which hybridizes to primer P5 overlaps a sequence which hybridizes to said 3' portion of primer P4.

12. The method according to claim 8 wherein said sequence which hybridizes to primer P5 is not adjacent to a sequence which hybridizes to said 3' portion of primer P4.

13. The method of claim 8 wherein either:
primer P2 is a mixture of primer P2 having a first label and primer P2 having a second label, or
primer P5 has a first label and primer P4 has a second label.

14. The method of claim 13 wherein said labels are selected from the group consisting of oligonucleotides, enzymes, dyes, fluorescent molecules, chemiluminescers, coenzymes, enzyme substrates, radioactive groups, small organic molecules and solid surfaces.

15. The method of claim 13 wherein the first label is the same as the second label.

16. A method of detecting the presence of a mutation in a target nucleic acid sequence comprising:
(a) combining in a reaction vessel to make a target mixture:
(1) the target sequence suspected of having the mutation;
(2) a primer P2 which hybridizes to a first strand of the target,
(3) a primer P5 which hybridizes to a second strand of the target,
(4) a primer P4 having a 3' region which hybridizes to said second strand of the target and a 5' tail region T which is not complementary to said second strand of the target, wherein a region on the second strand which hybridizes to the 3' region of P4 is located in the 5' direction of a region of the second strand which hybridizes to P5;
(5) a polymerase and nucleoside triphosphates;
(b) extending said primers along said target sequence;
(c) forming target partial duplexes having a tail of two non-complementary sequences said non-complementary sequences being P5 and T or the complements of P5 and T;
(d) combining in a reaction vessel to make a reference mixture:
(1) a reference nucleic acid sequence, said reference sequence being substantially identical to the target sequence but for the potential presence of the mutation in the target;
(2) said primer P2,
(3) said primer P5,
(4) said primer P4, and
(5) a polymerase and nucleoside triphosphates;
(e) extending said primers along the reference sequence;
(f) forming reference partial duplexes having a tail of two non-complementary sequences, said non-complementary sequences being P5 and T or the complements of P5 and T;
(g) combining said target partial duplexes with said reference partial duplexes;
(h) hybridizing the non-complementary tail sequences of the target partial duplex to the non-complementary tail sequences of the reference partial duplex to form a quadramolecular complex;
(i) subjecting said quadramolecular complex to strand exchange conditions wherein, if the difference exists between the target and the reference, strand exchange ceases, and wherein if no difference exists, strand exchange continues until complete strand exchange occurs;
(j) detecting the presence of said complex thereby detecting the presence of a mutation.

17. The method according to claim 16 wherein either:
primer P2 is a mixture of primer P2 having a first label and primer P2 having a second label, or
primer P4 has a first label and primer P5 has a second label;
and said presence of said complex is detected by determining the association of said labels.

18. The method of claim 17 wherein said labels are selected from the group consisting of oligonucleotides, enzymes, dyes, fluorescent molecules, chemiluminescers, coenzymes, enzyme substrates, radioactive groups, small organic molecules and solid surfaces.

19. The method of claim 17 wherein the association of said labels is detected by an induced luminescence assay.

20. The method according to claim 16 wherein the region which hybridizes to primer P5 is immediately adjacent said region which hybridizes to said 3' portion of primer P4.

21. The method according to claim 16 wherein the region which hybridizes to primer P5 overlaps said region which hybridizes to said 3' portion of primer P4.

22. The method according to claim 16 wherein the region which hybridizes to primer P5 is not adjacent to said region which hybridizes to said 3' portion of primer P4.

23. The method according to claim 16 wherein said target mixture and the reference mixture are combined in the same reaction vessel.

24. The method according to claim 17 wherein the first label is the same as the second label.

25. In a method for detecting the presence of a difference between a target nucleic acid sequence and a reference nucleic acid sequence, wherein said difference is detected by the presence quadramolecular complex comprising a tailed partial duplex of the target sequence and a tailed partial duplex of the reference strand, the improvement comprising:

forming the tailed target partial duplex and the tailed reference partial duplex by amplifying the target and the reference nucleic acid sequences by polymerase chain reaction using primer P2, a primer P4 having a 3' portion which hybridizes to the target sequence or the reference sequence and a 5' tail portion T which is not complementary to the target sequence or the reference sequence, and a primer P5 which hybridizes to the target sequence or the reference sequence at a location in the 3' direction from a sequence which hybridizes to said 3' portion of primer P4.

26. A quadramolecular complex of a double stranded nucleic acid target sequence having a mutation and a double stranded nucleic acid reference sequence, the complex being made by the steps comprising:

(a) amplifying the target and the reference nucleic acid sequences by polymerase chain reaction using primer P2, a primer P4 having a 3' portion which hybridizes to the reference sequence and a 5' tail portion T which is not complementary to the target sequence or the reference sequence, and a primer P5 which hybridizes to the target sequence or the reference sequence at a location in the 3' direction from a sequence which hybridizes to said 3' portion of primer P4;

(b) forming partial duplexes of the target sequence and the reference sequence having tails of two non-complementary strands wherein a first strand is the sequence P5 or its complement and the second strand is the sequence T or its complement, and (c) hybridizing said strands of said tail of the reference partial duplex with said strands of said tails of the target partial duplex to form said quadramolecular complex.

27. The quadramolecular complex of claim 26 wherein the complex is detectable due to the presence of labels on the non-complementary strands of the target and reference sequences, and further wherein either:

Primer P2 is a mixture of primer P2 having a first label and primer P2 having a second label, or primer P4 has a first label and primer P5 has a second label.

* * * * *

SEQUENCE LISTING

<160> NUMBER OF SEQ ID NOS: 23

<210> SEQ ID NO: 1
<211> LENGTH: 20
<212> TYPE: DNA
<213> ORGANISM: Human

<400> SEQUENCE: 1
caagtgaatc ctgagcgtga                                          20

<210> SEQ ID NO: 2
<211> LENGTH: 22
<212> TYPE: DNA
<213> ORGANISM: Human

<400> SEQUENCE: 2
ctaaccgatt gaatatggag cc                                       22

<210> SEQ ID NO: 3
<211> LENGTH: 22
<212> TYPE: DNA
<213> ORGANISM: Human

<400> SEQUENCE: 3
ctcagttttc ctggattatg cc                                       22

<210> SEQ ID NO: 4
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 4
accatgctcg agattacgag ctaaccgatt gaatatggag cc                 42

<210> SEQ ID NO: 5
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 5
gatcctaggc ctcacgtatt ctaaccgatt gaatatggag cc                 42

<210> SEQ ID NO: 6
<211> LENGTH: 22
<212> TYPE: DNA
<213> ORGANISM: Human

<400> SEQUENCE: 6
tagaaggaag atgtgccttt ca                                       22

<210> SEQ ID NO: 7
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 7
accatgctcg agattacgag ttcttaaccc actagccata aa        42

<210> SEQ ID NO: 8
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 8
gatcctaggc ctcacgtatt ttcttaaccc actagccata aa        42

<210> SEQ ID NO: 9
<211> LENGTH: 24
<212> TYPE: DNA
<213> ORGANISM: Artificial Sequence
<220> FEATURE:
<221> NAME/KEY: primer_bind
<222> LOCATION: (1)...(24)

<400> SEQUENCE: 9
ttacattaga aggaagatgt gcct        24

<210> SEQ ID NO: 10
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 10
accatgctcg agattacgag gtgattctta acccactagc ca        42

<210> SEQ ID NO: 11
<211> LENGTH: 42
<212> TYPE: DNA
<213> ORGANISM: Artificial Sequence
<220> FEATURE:
<221> NAME/KEY: primer_bind
<222> LOCATION: (1)...(42)

<400> SEQUENCE: 11
gatcctaggc ctcacgtatt gtgattctta acccactagc ca        42

<210> SEQ ID NO: 12
<211> LENGTH: 44
<212> TYPE: DNA
<213> ORGANISM: Artificial Sequence
<220> FEATURE:
<221> NAME/KEY: primer_bind
<222> LOCATION: (1)...(44)

<400> SEQUENCE: 12
agcctaatcg tccacgatgt ataaatatat aatttgggta gtgt        44

<210> SEQ ID NO: 13
<211> LENGTH: 22
<212> TYPE: DNA
<213> ORGANISM: Artificial Sequence
<220> FEATURE:
<221> NAME/KEY: primer_bind
<222> LOCATION: (1)...(22)

<400> SEQUENCE: 13
ctaaccgatt gaatatggag cc                                    22

<210> SEQ ID NO: 14
<211> LENGTH: 22
<212> TYPE: DNA
<213> ORGANISM: Human

<400> SEQUENCE: 14
gcctttcaaa ttcagattga gc                                    22

<210> SEQ ID NO: 15
<211> LENGTH: 22
<212> TYPE: DNA
<213> ORGANISM: Human

<400> SEQUENCE: 15
gacatttaca gcaaatgctt gc                                    22

<210> SEQ ID NO: 16
<211> LENGTH: 44
<212> TYPE: DNA
<213> ORGANISM: Human

<400> SEQUENCE: 16
agacgacgtc tagtcattcg aatagaccaa taattagtta ttca            44

<210> SEQ ID NO: 17
<211> LENGTH: 24
<212> TYPE: DNA
<213> ORGANISM: Artificial Sequence
<220> FEATURE:
<221> NAME/KEY: primer_bind
<222> LOCATION: (1)...(24)

<400> SEQUENCE: 17
caactgtggt taaagcaata gtgt                                  24

<210> SEQ ID NO: 18
<211> LENGTH: 24
<212> TYPE: DNA
<213> ORGANISM: Human

<400> SEQUENCE: 18
gcacagattc tgagtaacca taat                                  24

<210> SEQ ID NO: 19
<211> LENGTH: 48
<212> TYPE: DNA
<213> ORGANISM: Human

<400> SEQUENCE: 19
atgacttgct aagtgctatg actcctctac caaatctgga tactatac        48

<210> SEQ ID NO: 20
<211> LENGTH: 44

```
-continued

<212> TYPE: DNA
<213> ORGANISM: Artificial Sequence
<220> FEATURE:
<221> NAME/KEY: primer_bind
<222> LOCATION: (1)...(44)

<400> SEQUENCE: 20
agcctaatcg tccacgatgt ataaatatat aatttgggta gtgt              44

<210> SEQ ID NO: 21
<211> LENGTH: 41
<212> TYPE: DNA
<213> ORGANISM: Artificial Sequence
<220> FEATURE:
<221> NAME/KEY: primer_bind
<222> LOCATION: (1)...(41)

<400> SEQUENCE: 21
agcctaatcg tccacgatgt atgtagtgtg aagggttcat a                 41

<210> SEQ ID NO: 22
<211> LENGTH: 41
<212> TYPE: DNA
<213> ORGANISM: Artificial Sequence
<220> FEATURE:
<221> NAME/KEY: primer_bind
<222> LOCATION: (1)...(41)

<400> SEQUENCE: 22
agcctaatcg tccacgatgt attggagcca aatatataat t                 41

<210> SEQ ID NO: 23
<211> LENGTH: 22
<212> TYPE: DNA
<213> ORGANISM: Human

<400> SEQUENCE: 23
ctaaccgatt gaatatggag cc                                      22
```